(12) United States Patent
Loccufier et al.

(10) Patent No.: US 8,492,452 B2
(45) Date of Patent: *Jul. 23, 2013

(54) POLYMERIZABLE PHOTOINITIATORS AND RADIATION CURABLE COMPOSITIONS

(75) Inventors: Johan Loccufier, Zwijnaarde (BE); Luc Van Maele, Lochristi (BE); Jaymes Van Luppen, Wilrijk (BE); Roland Claes, Dendermonde (BE)

(73) Assignee: Agfa Graphics NV, Mortsel (BE)

( * ) Notice: Subject to any disclaimer, the term of this patent is extended or adjusted under 35 U.S.C. 154(b) by 118 days.

This patent is subject to a terminal disclaimer.

(21) Appl. No.: 13/129,413

(22) PCT Filed: Dec. 1, 2009

(86) PCT No.: PCT/EP2009/066155
§ 371 (c)(1),
(2), (4) Date: May 16, 2011

(87) PCT Pub. No.: WO2010/069758
PCT Pub. Date: Jun. 24, 2010

(65) Prior Publication Data
US 2011/0224324 A1    Sep. 15, 2011

Related U.S. Application Data

(60) Provisional application No. 61/138,955, filed on Dec. 19, 2008.

(30) Foreign Application Priority Data

Dec. 18, 2008 (EP) .................................. 08172104

(51) Int. Cl.
C08F 2/50 (2006.01)
C08J 3/28 (2006.01)

(52) U.S. Cl.
USPC ............... 522/34; 522/35; 522/904; 522/905; 522/113; 522/114; 522/120; 522/121; 522/150; 522/153; 522/178; 522/182; 549/27; 560/53; 560/149; 560/228; 560/221; 560/213; 558/87; 558/179

(58) Field of Classification Search
USPC ............. 522/35, 34, 904, 905, 113, 114, 120, 522/121, 150, 153, 178, 182; 549/27; 560/53, 560/149, 228, 221, 213; 558/87, 179
See application file for complete search history.

(56) References Cited

U.S. PATENT DOCUMENTS

2006/0142408 A1    6/2006  Liu et al.
2011/0159203 A1*   6/2011  Loccufier et al. ............. 427/532

FOREIGN PATENT DOCUMENTS

| CA | 1 180 486 A | 1/1985 |
|---|---|---|
| CA | 2 005 283 C | 2/2001 |
| EP | 0 217 205 A2 | 4/1987 |
| EP | 1 616 921 A1 | 1/2006 |
| EP | 1 674 499 A1 | 6/2006 |
| GB | 925117 | 5/1963 |
| JP | 2002-187868 A | 7/2002 |
| JP | 2004-224993 A | 8/2004 |
| JP | 2005-082679 A | 3/2005 |
| WO | 95/10552 A1 | 4/1995 |
| WO | 03/033492 A1 | 4/2003 |
| WO | 03/068785 A1 | 8/2003 |
| WO | 2004/103580 A1 | 12/2004 |
| WO | 2006/056541 A1 | 6/2006 |
| WO | 2009/068590 A1 | 6/2009 |

OTHER PUBLICATIONS

Vysotskaya et al., "Functional Acetal Methacrylates: III. Electrophilic Addition of Diols to 2-(Vinyloxy)ethyl Methacrylate", Russian Journal of Organic Chemistry, vol. 38, No. 8, 2002, pp. 1133-1138.
Official Communication issued in International Patent Application No. PCT/EP2009/066155, mailed on Feb. 5, 2010.

* cited by examiner

Primary Examiner — Sanza McClendon
(74) Attorney, Agent, or Firm — Keating & Bennett, LLP

(57) ABSTRACT

A polymerizable photoinitiator is represented by Formula (I):

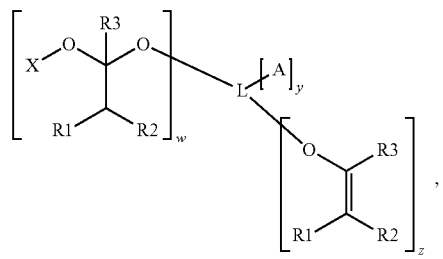

Formula (I)

wherein R1, R2 and R3 are independently selected from the group consisting of a hydrogen, an optionally substituted alkyl group and an optionally substituted aryl group or R1 and R3 represent the necessary atoms to form a five to eight membered ring; p, w, y and z are all integers with y representing a value 1 to 6; p representing the sum of w and z; p representing a value of 1 to 6; w=1 to (p−z) and z=0 to (p−w); L represents an optionally substituted (p+y)-valent linking group comprising 1 to 14 carbon atoms; A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, an allyl ester group and a vinyl ester group; and X represents a photoinitiating moiety including at least one group capable of initiating a free radical polymerization reaction upon exposure to actinic radiation.

26 Claims, No Drawings

POLYMERIZABLE PHOTOINITIATORS AND RADIATION CURABLE COMPOSITIONS

CROSS-REFERENCE TO RELATED APPLICATIONS

This application is a 371 National Stage Application of PCT/EP2009/066155, filed Dec. 1, 2009. This application claims the benefit of U.S. Provisional Application No. 61/138,955, filed Dec. 19, 2008, which is incorporated by reference herein in its entirety. In addition, this application claims the benefit of European Application No. 08172104.5, filed Dec. 18, 2008, which is also incorporated by reference herein in its entirety.

BACKGROUND OF THE INVENTION

1. Field of the Invention

The present invention relates to a new class of polymerizable photoinitiators, especially suitable for food compliant radiation curable formulations, and methods for preparing the photoinitiators.

2. Description of the Related Art

A free radical photoinitiator initiates the polymerization of monomers when exposed to actinic radiation by the formation of a free radical. Photoinitiators are frequently used in UV-curable compositions, such as UV-curable inkjet inks.

Two types of free radical photoinitiators can be distinguished. A Norrish Type I initiator is an initiator which cleaves after excitation, yielding the initiating radical immediately. A Norrish Type II-initiator is a photoinitiator which is activated by actinic radiation and forms free radicals by hydrogen abstraction from a second compound that becomes the actual initiating free radical. This second compound is called a co-initiator or polymerization synergist.

A photoinitiator can be a monofunctional compound, but can also be a multifunctional compound, i.e. having more than one photoinitiating group. WO 03/033492 (COATES BROTHERS) discloses multifunctional thioxanthone photoinitiators.

When radiation curable compositions are used for food packaging, toys and dental applications, the amount of extractable residues is a critical issue and needs to be minimized. Low molecular weight compounds are usually not completely built into the polymer network and are prone to be readily extracted or to diffuse out of the cured composition. Therefore, it is a continuous concern to design photoinitiators having a reduced tendency to be extracted or to migrate out of the cured composition.

One approach to minimize the extraction of photoinitiators is the use of photoinitiators with a higher molecular weight. However, polymeric initiators have a tendency to lose reactivity. Hence, often considerable amounts of polymeric initiators are required in order to reach the desired curing speed, thereby also increasing the viscosity to an undesirable level for a great number of applications using radiation curable compositions, such as e.g. inkjet printing. To overcome the undesirable viscosity increase of radiation curable compositions, EP 1616921 A (AGFA GRAPHICS) and EP 1674499 A (AGFA GRAPHICS) disclose radiation curable compositions comprising polymeric photoinitiators, comprising a dendritic polymer core. While the use of a dendritic polymer core is advantageous for maintaining a low viscosity of the radiation curable composition, a further improvement in curing speed is desirable, especially in the absence of nitrogen inertisation.

Another approach in solving the extraction problem is the design of a photoinitiator having one or more ethylenically unsaturated polymerizable groups so that it can be copolymerized with the other monomers of the radiation curable composition. Numerous photoinitiators comprising an ethylenically unsaturated polymerizable group have been disclosed in the literature, for use in radiation curable compositions or as a monomer for the preparation of polymeric photoinitiators.

JP 2004-224993 (NIPPON KAYAKY) discloses self-photopolymerization type photopolymerization initiators for reducing its evaporation or sublimation from cured films of radiation curable compositions. Other (meth)acrylated thioxanthones have been disclosed in, for example, CA 2005283 (BASF) and CA 1180486 (CIBA).

(Meth)acrylated benzophenones are disclosed in, for example, US 2006/0142408 (NATIONAL STARCH) and GB 925117 (DU PONT).

(Meth)acrylated a-hydroxy-ketones are disclosed in, for example, WO 2005/108452 (ASHLAND), WO 97/17378 (COATES BROTHERS) and EP 538553 A (HUGHES AIRCRAFT).

(Meth)acrylated a-amino ketones are disclosed in, for example, WO 96/20919 (CIBA) and CA 2005283 (BASF).

(Meth)acrylated acyl phosphine oxide initiators are disclosed in, for example, WO 2006/056541 (CIBA), WO 2004/103580 (CIBA) and AU 2003205731 (BASF).

(Meth)acrylated benzil dialkyl acetals are disclosed in JP 2005-082679 (DAINIPPON INK).

Often, the synthesis of the target photoinitiators requires the use of (meth)acryloyl chloride. It is commonly known that (meth)acryloyl chloride is highly reactive and limited in stability. It is often contaminated with cyclic dimers (see for example in JP 2002-187868 (DAICEL CHEMICAL)) thus requiring distillation prior to use. Combined with the highly toxic nature of (meth)acryloyl chloride, the limited availability on the market and the high cost, synthetic methods using (meth)acryloyl chloride are not well suited for the preparation of (meth)acrylated photoinitiators on an industrial scale.

PCT/EP2008/066289 (AGFA GRAPHICS) discloses an optimized synthetic method for the preparation of acrylated or methacrylated photoinitiators. Though avoiding highly toxic and unstable reagents, an isolation procedure is still required to obtain high purity (meth)acrylated photoinitiators, suitable for food packaging applications, generating additional costs in production and increasing the ecological footprint.

Therefore, there is still a need for photoinitiators, having a significantly reduced tendency to be extracted or migrate out of the cured composition, having a good compatibility with a wide variety of radiation curable formulations and accessible via a simple and cost efficient synthetic procedure having a reduced ecological footprint.

SUMMARY OF THE INVENTION

Preferred embodiments of the present invention provide a new class of polymerizable photoinitiators accessible via a simple and cost efficient synthetic procedure.

Another preferred embodiment of the present invention provides a radiation curable composition including such a polymerizable photoinitiator.

Another preferred embodiment of the present invention provides a radiation curable ink and a radiation curable inkjet ink including such a polymerizable photoinitiator.

These and other preferred embodiments of the present invention will become apparent in the detailed description hereinafter.

A surprisingly simple method was found to solve the above cited problems by preparing a polymerizable photoinitiator requiring no isolation, through the reaction of a photoinitiator having at least one hydroxyl group with a specific monomer in the presence of a catalyst. No organic solvents are necessary, thereby avoiding the unecological removal of solvents. This allows e.g. radiation curable inkjet inks lacking organic solvents, which as a consequence exhibit an improved jetting performance in the printer by improved latency and less failing nozzles.

Solubility problems of an isolated photopolymerizable photoinitiator in a radiation curable composition can also be avoided by simply removing the catalyst and using the polymerizable photoinitiator dissolved in the specific monomer as such for addition to a radiation curable composition.

Preferred embodiments of the present invention have been realized with a polymerizable photoinitiator as defined below.

Further advantages and preferred embodiments of the present invention will become apparent from the following description.

DETAILED DESCRIPTION OF THE PREFERRED EMBODIMENTS

Definitions

The term "dye", as used in disclosing the present invention, means a colorant having a solubility of 10 mg/L or more in the medium in which it is applied and under the ambient conditions pertaining.

The term "pigment" is defined in DIN 55943, herein incorporated by reference, as a colorant that is practically insoluble in the application medium under the pertaining ambient conditions, hence having a solubility of less than 10 mg/L therein.

The term "C.I." is used in disclosing the present application as an abbreviation for Color Index.

The term "alkyl" means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methylbutyl etc.

Polymerizable Initiators

The polymerizable photoinitiator according to a preferred embodiment of the present invention is represented by Formula (I):

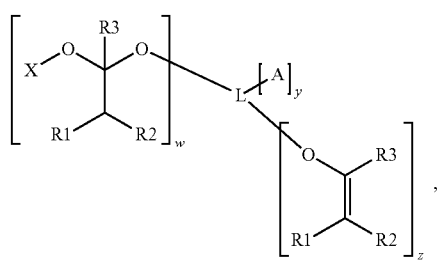

Formula (I)

wherein

R1, R2 and R3 are independently selected from the group consisting of a hydrogen, an optionally substituted alkyl group and an optionally substituted aryl group or R1 and R3 represent the necessary atoms to form a five to eight membered ring;

p, w, y and z are all integers with y representing a value 1 to 6; p representing the sum of w and z; p representing a value of 1 to 6; w=1 to (p−z) and z=0 to (p−w);

L represents an optionally substituted (p+y)-valent linking group comprising 1 to 14 carbon atoms;

A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, an allyl ester group and a vinyl ester group; and X represents a photoinitiating moiety comprising at least one group capable of initiating a free radical polymerization reaction upon exposure to actinic radiation.

In a preferred embodiment, the radically polymerizable group A is selected from the group consisting of an acrylate and a methacrylate, an acrylate being particularly preferred.

In a further preferred embodiment R2 and R3 both represent hydrogen.

In a preferred embodiment R1 represents hydrogen.

In a more preferred embodiment R1, R2 and R3 all represent hydrogen.

In a preferred embodiment, the divalent linking group L is selected from the group consisting of an optionally substituted alkylene group and an aliphatic ether containing group.

In a preferred embodiment, y represents a value 1 to 4, more preferably y represents a value 2 to 3.

In a preferred embodiment, p represents a value 1 to 4, more preferably p represents a value 2 to 3.

In a preferred embodiment, z represents a value of 0.

A preferred divalent linking group L is —(—CH$_2$—CH$_2$—O—)$_n$—CH$_2$—CH$_2$— with n being an integer equal to 1, 2, 3, 4, 5 or 6.

A preferred divalent linking group L is —(—CH$_2$—)$_n$— with n being an integer equal to 1 to 14, more preferably n is equal to 1, 2, 3, 4, 5 or 6.

In a preferred embodiment, the photoinitiating moiety X comprises at least one group selected from the group consisting of an optionally substituted benzophenone group, an optionally substituted thioxanthone group, a substituted or unsubstituted anthraquinone group, a camphor quinone group, an α-hydroxyalkylphenone group, an α-aminoalkylphenone group, an acylphosphine oxide group, a bisacyl phosphine oxide group, an acylphosphine sulfide group, a phenyl glyoxalate group, a benzoin ether group, a benzyl ketal group, an α-dialkoxyacetophenone group, a carbazolyl-O-acyl-oxime group, an α-haloarylketone group and an α-haloaryl sulfone group.

In a preferred embodiment, the photoinitiating moiety X is a α-hydroxyalkylphenone group.

In a preferred embodiment, the photoinitiating moiety X is a substituted benzophenone group or an unsubstituted benzophenone group.

In a preferred embodiment, the photoinitiating moiety X is a substituted thioxanthone group or an unsubstituted thioxanthone group.

In a preferred embodiment y=1, w=1 and z=0.
In another preferred embodiment y=1, w=2 and z=0.
In another preferred embodiment y=2, w=1 and z=0.
In another preferred embodiment y=2, w=2 and z=0.

In a preferred embodiment, the polymerizable photoinitiators according to the present invention are photoinitiators according to Formula (Ib):

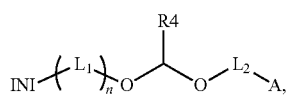

Formula (Ib)

wherein

INI represents a group selected from the group consisting of an optionally substituted benzophenone group, an optionally substituted thioxanthone group, a substituted or unsubstituted anthraquinone group, a camphor quinone group, an α-hydroxyalkylphenone group, an α-aminoalkylphenone group, an acylphosphine oxide group, a bisacyl phosphine oxide group, an acylphosphine sulfide group, a phenyl glyoxalate group, a benzoin ether group, a benzyl ketal group, an α-dialkoxy-acetophenone group, a carbazolyl-O-acyl-oxime group, an α-haloarylketone group and an α-haloaryl sulfone group;

$L_1$ and $L_2$ independently represent a substituted or unsubstituted divalent linking group comprising 1 to 14 carbon atoms;

A represents a radically polymerizable functional group selected from the group consisting of an acrylate, a methacrylate, a styrene, an acryl amide, a methacryl amide, a maleate, a fumarate, an itaconate, an vinyl ether, an allyl ether, an allyl ester and a vinyl ester;

n represents 0 or 1; and

R4 represents an optionally substituted alkyl group.

In a preferred embodiment, A is selected from the group consisting of an acrylate and a methacrylate.

In a most preferred embodiment, R4 represents a methyl group.

In a further preferred embodiment, $L_2$ is selected from the group consisting of a substituted alkylene group, an unsubstituted alkylene group and an aliphatic ether containing group.

Typical photoinitiators according to Formulas (I) and (Ib) are given in Table 1, without being limited thereto.

TABLE 1

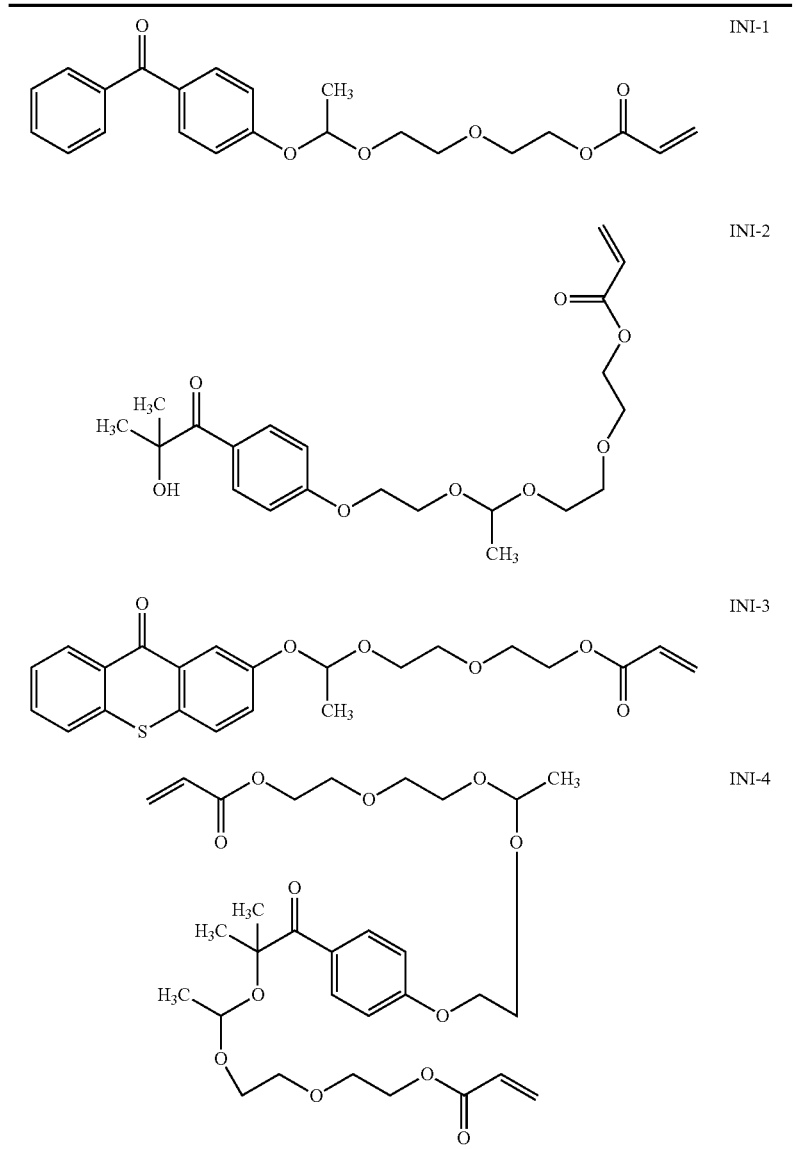

TABLE 1-continued
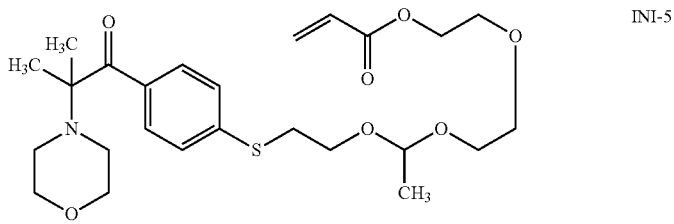
INI-5
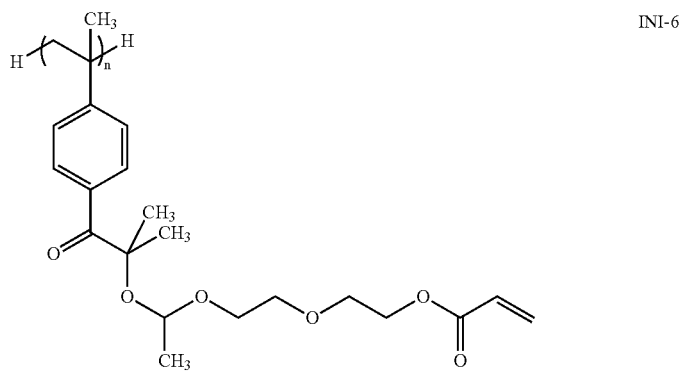
INI-6
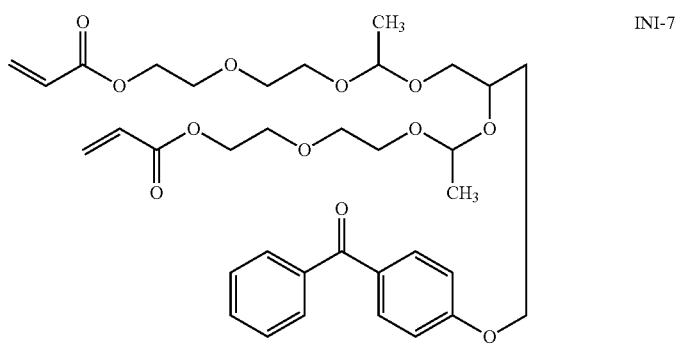
INI-7
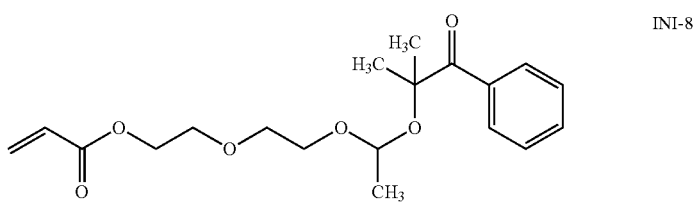
INI-8
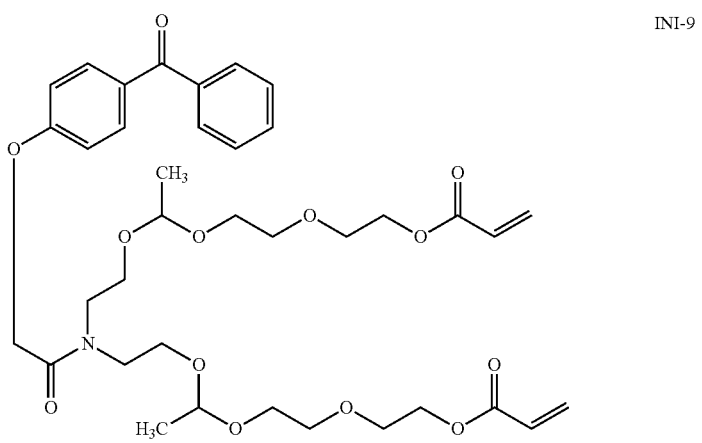
INI-9

TABLE 1-continued
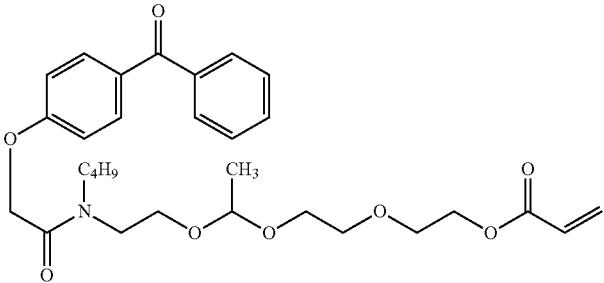
INI-10
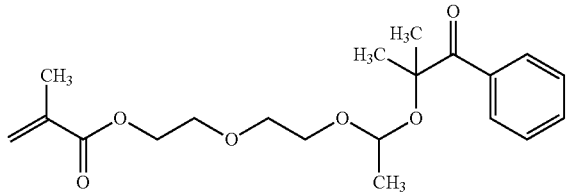 [SMILES: C=C(C)C(=O)OCCOCCOC(C)OC(C)(C)C(=O)c1ccccc1]
INI-11
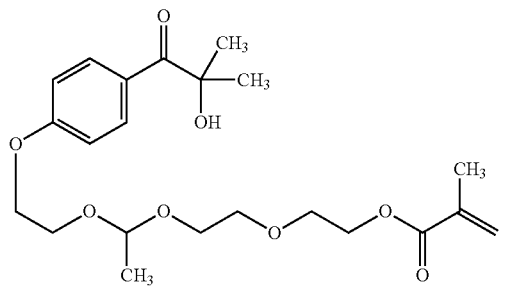 [SMILES: C=C(C)C(=O)OCCOCCOC(C)OCCOc1ccc(C(=O)C(C)(C)O)cc1]
INI-12
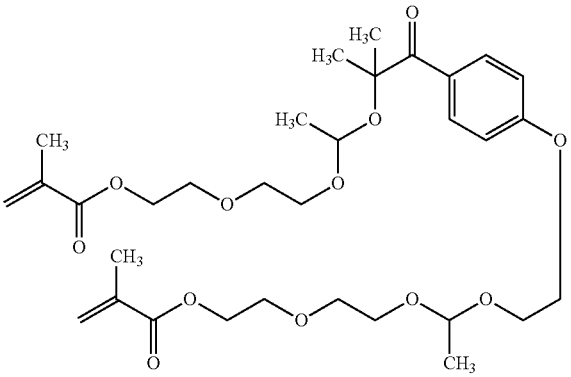 [SMILES: C=C(C)C(=O)OCCOCCOC(C)OCCOc1ccc(C(=O)C(C)(C)OC(C)OCCOCCOC(=O)C(=C)C)cc1]
INI-13
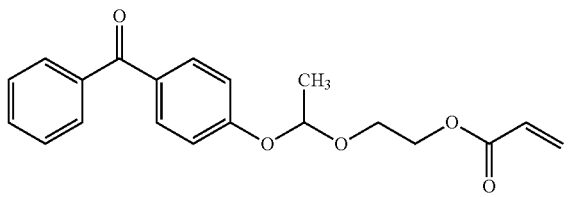 [SMILES: C=CC(=O)OCCOC(C)Oc1ccc(C(=O)c2ccccc2)cc1]
INI-14
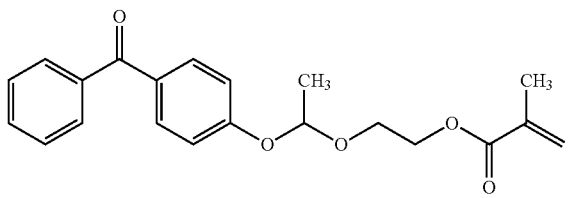 [SMILES: C=C(C)C(=O)OCCOC(C)Oc1ccc(C(=O)c2ccccc2)cc1]
INI-15

TABLE 1-continued
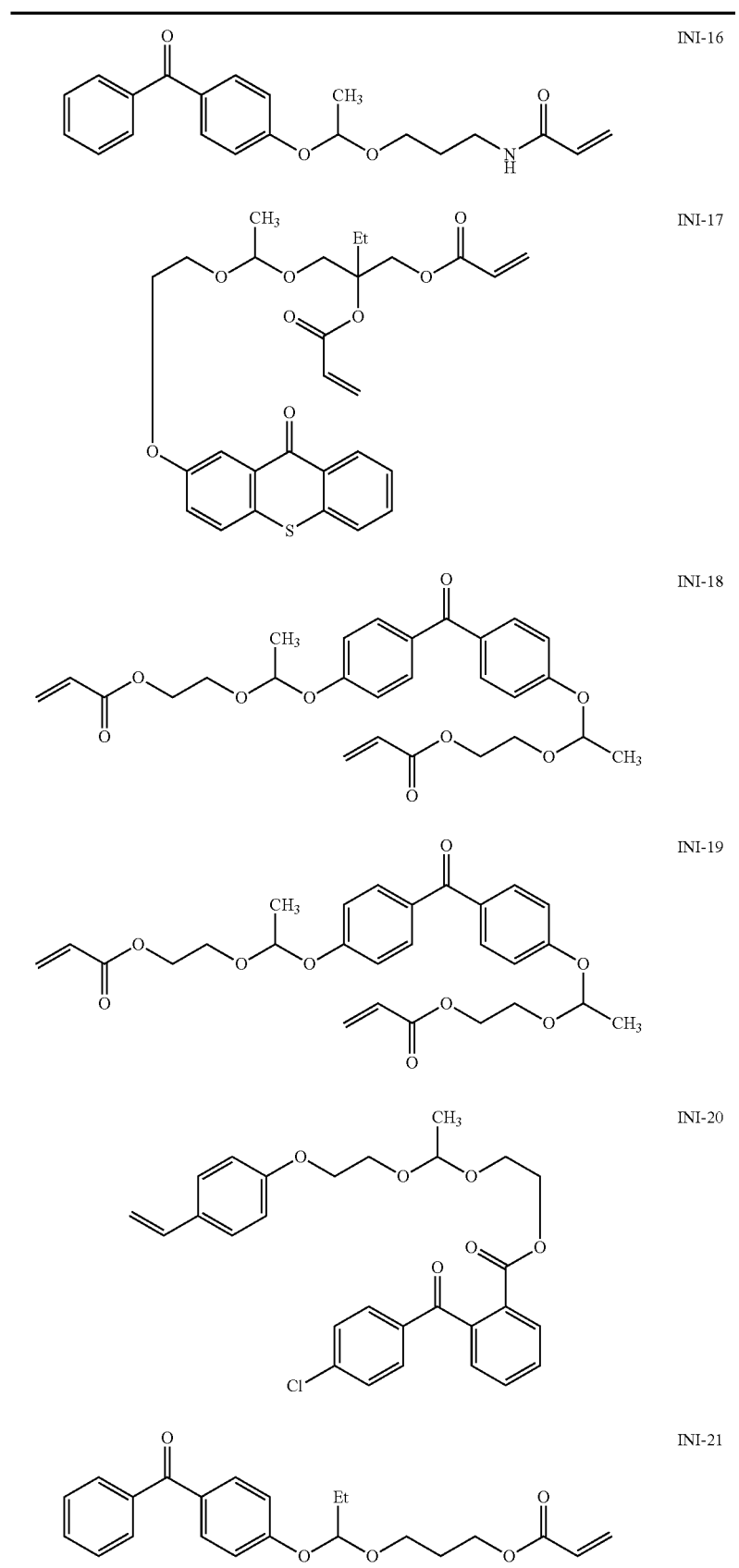

TABLE 1-continued
| | |
|---|---|
| 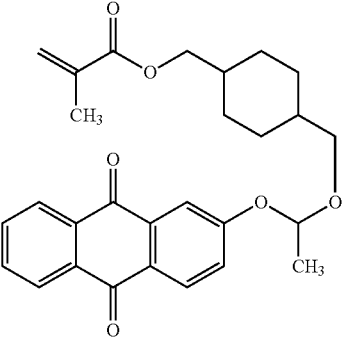 [SMILES: C=C(C)C(=O)OCC1CCC(COC(C)Oc2ccc3c(c2)C(=O)c2ccccc2C3=O)CC1] | INI-22 |
| 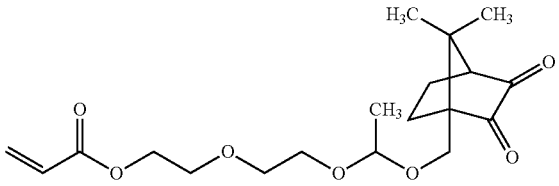 [SMILES: C=CC(=O)OCCOCCOC(C)OCC12CCC(C(=O)C1=O)C2(C)C] | INI-23 |
| 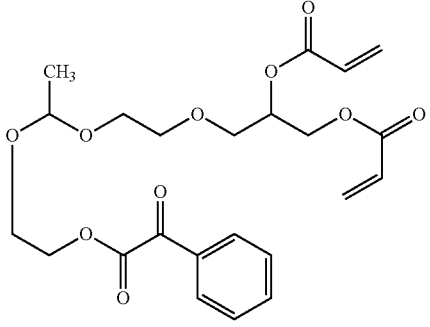 [SMILES: C=CC(=O)OCC(COCCOC(C)OCCOC(=O)C(=O)c1ccccc1)OC(=O)C=C] | INI-24 |
| 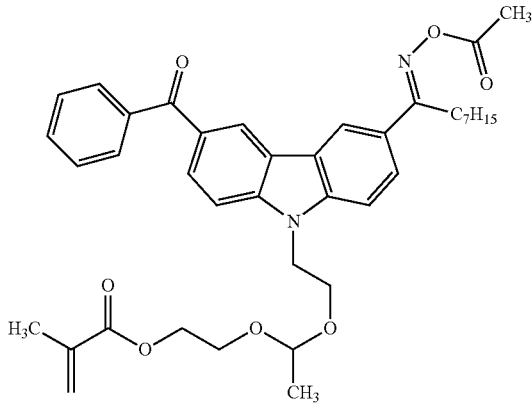 | INI-25 |
| 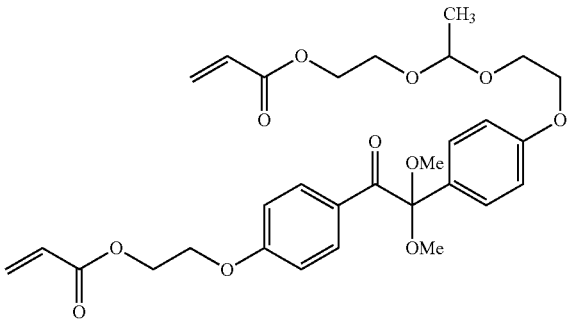 [SMILES: C=CC(=O)OCCOc1ccc(C(=O)C(OC)(OC)c2ccc(OCCOC(C)OCCOC(=O)C=C)cc2)cc1] | INI-26 |

TABLE 1-continued
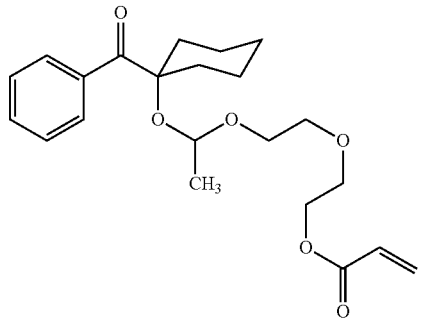 [SMILES: C=CC(=O)OCCOCCOC(C)OC1(C(=O)c2ccccc2)CCCCC1]
INI-27
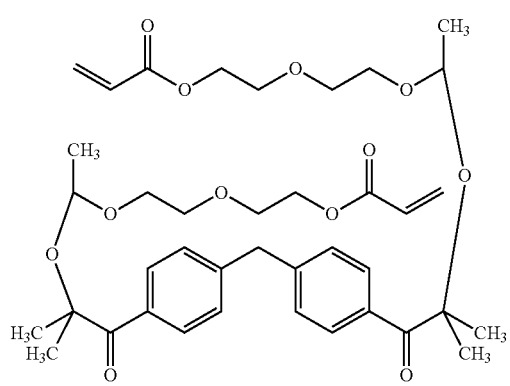 [SMILES: C=CC(=O)OCCOCCOC(C)OC(C)(C)C(=O)c1ccc(Cc2ccc(C(=O)C(C)(C)OC(C)OCCOCCOC(=O)C=C)cc2)cc1]
INI-28
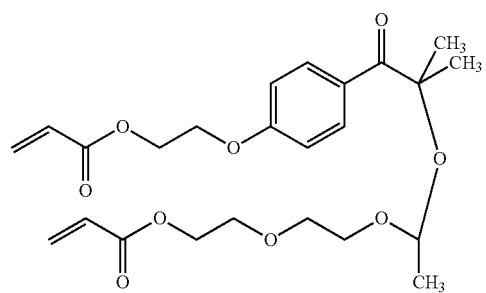 [SMILES: C=CC(=O)OCCOCCOC(C)OC(C)(C)C(=O)c1ccc(OCCOC(=O)C=C)cc1]
INI-29
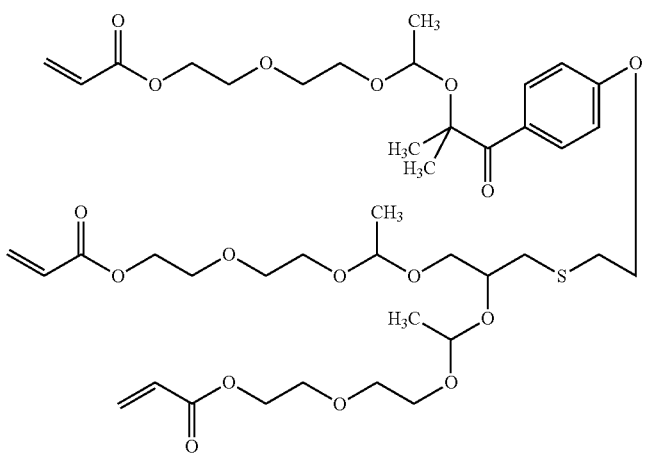 [SMILES: C=CC(=O)OCCOCCOC(C)OCC(CSCCOc1ccc(C(=O)C(C)(C)OC(C)OCCOCCOC(=O)C=C)cc1)OC(C)OCCOCCOC(=O)C=C]
INI-30

TABLE 1-continued
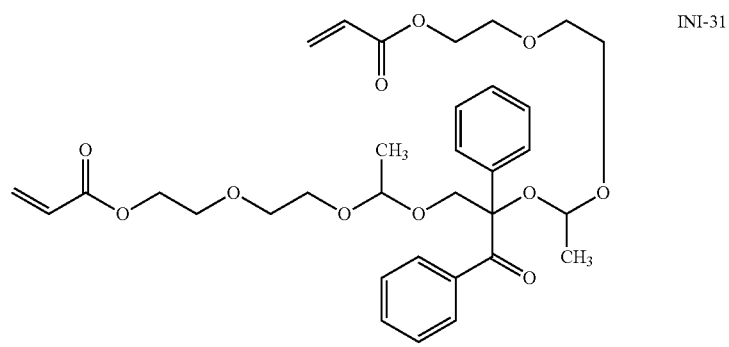
INI-31
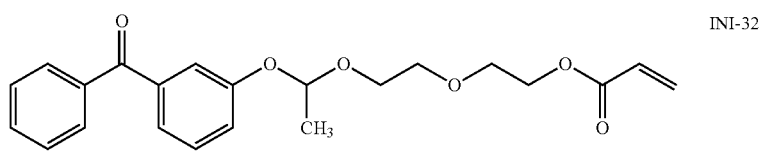
INI-32
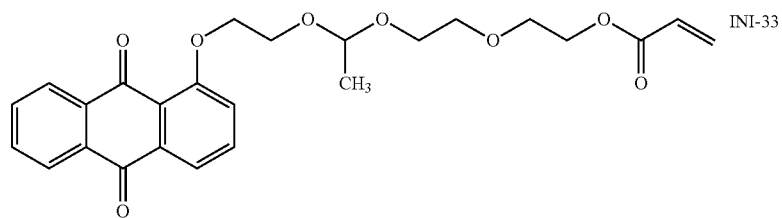
INI-33
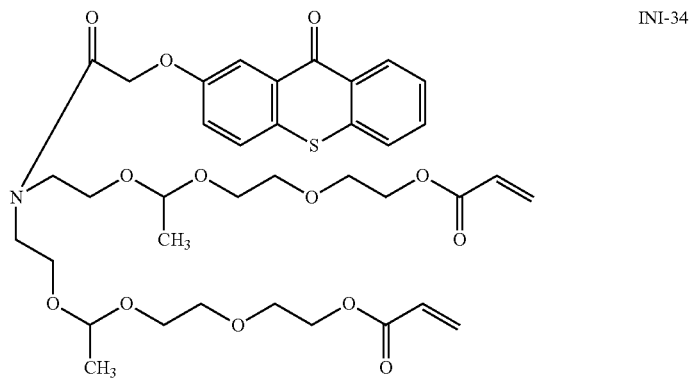
INI-34
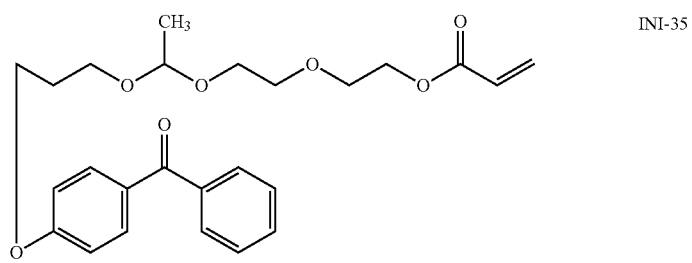
INI-35

TABLE 1-continued
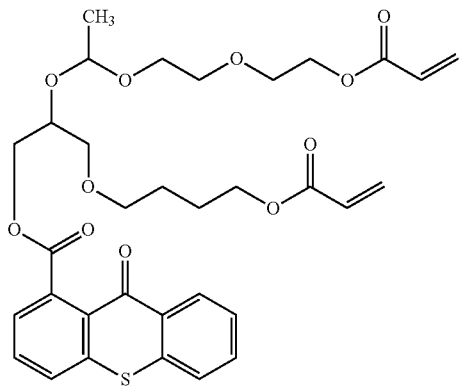 [SMILES: C=CC(=O)OCCCCOCC(COC(=O)c1cccc2sc3ccccc3c(=O)c12)OC(C)OCCOCCOC(=O)C=C]
INI-36
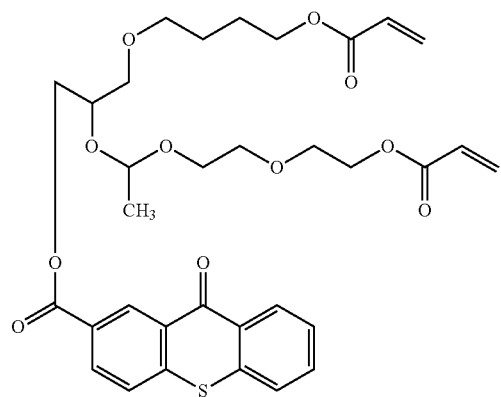 [SMILES: C=CC(=O)OCCCCOCC(COC(=O)c1ccc2sc3ccccc3c(=O)c2c1)OC(C)OCCOCCOC(=O)C=C]
INI-37
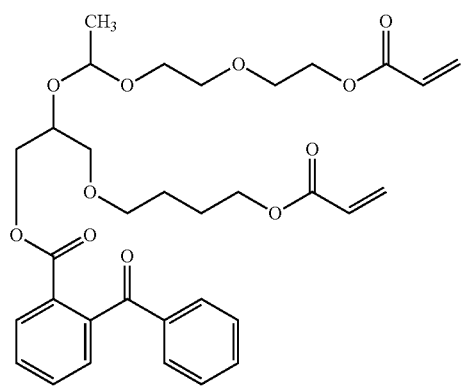 [SMILES: C=CC(=O)OCCCCOCC(COC(=O)c1ccccc1C(=O)c1ccccc1)OC(C)OCCOCCOC(=O)C=C]
INI-38
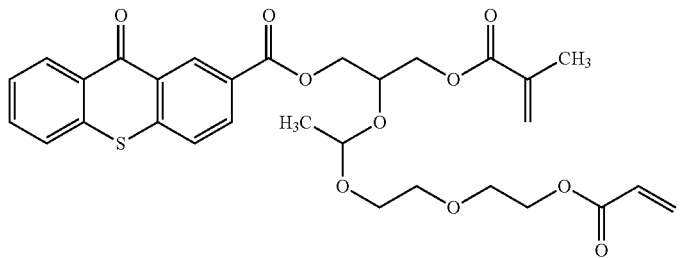 [SMILES: C=CC(=O)OCCOCCOC(C)OC(COC(=O)C(=C)C)COC(=O)c1ccc2sc3ccccc3c(=O)c2c1]
INI-39

TABLE 1-continued
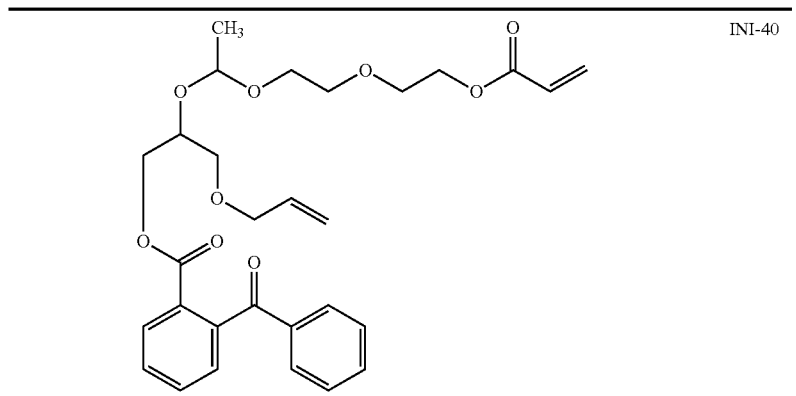
INI-40
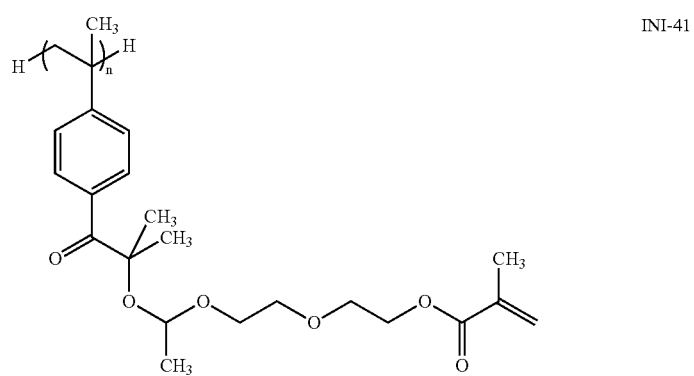
INI-41
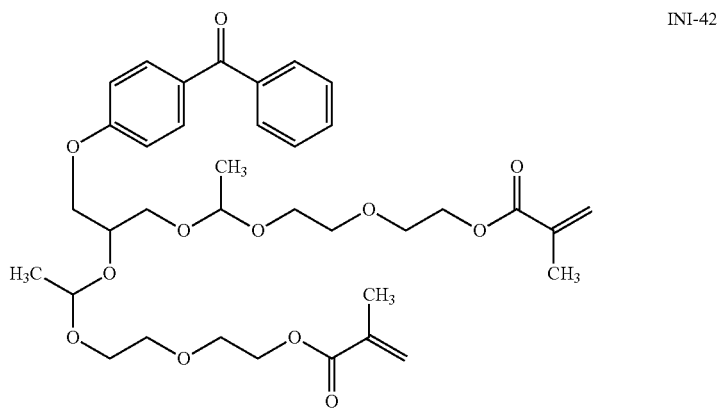
INI-42
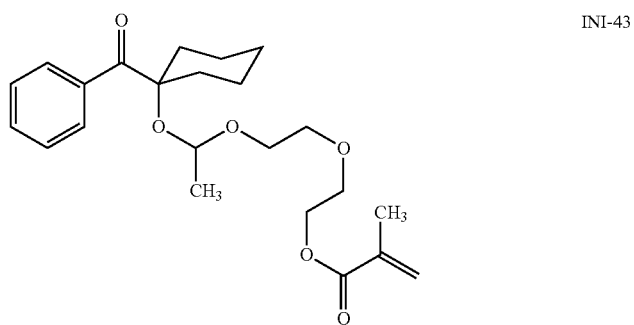
INI-43

TABLE 1-continued

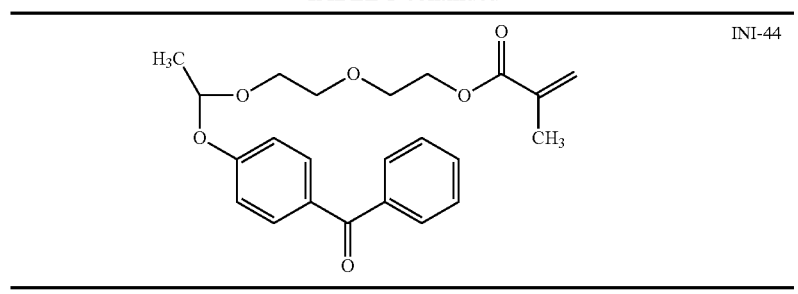

INI-44

Monomers of Formula (II)

For preparing the polymerizable photoinitiator according to a preferred embodiment of the present invention, at least one monomer according to Formula (II) is used:

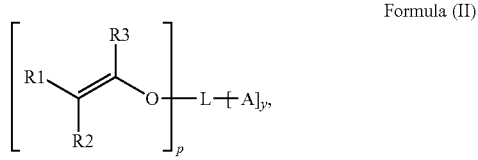

Formula (II)

wherein
R1, R2 and R3 are independently selected from the group consisting of a hydrogen, an optionally substituted alkyl group and an optionally substituted aryl group or R1 and R3 represent the necessary atoms to form a five to eight membered ring;
p is an integer having a value of 1 to 6;
y is an integer having a value of 1 to 6;
L represents an optionally substituted (p+y)-valent linking group comprising 1 to 14 carbon atoms; and
A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, an allyl ester group and a vinyl ester group.

In a preferred embodiment, the radically polymerizable group A is selected from the group consisting of an acrylate and a methacrylate, an acrylate being particularly preferred.

In a further preferred embodiment R2 and R3 both represent hydrogen.

In a preferred embodiment R1 represents hydrogen.

In a more preferred embodiment R1, R2 and R3 all represent hydrogen.

In a preferred embodiment, the divalent linking group L is selected from the group consisting of an optionally substituted alkylene group and an aliphatic ether containing group.

A preferred divalent linking group L is —(—CH2-CH2-O—)n-CH2—CH2- with n being an integer equal to 1, 2, 3, 4, 5 or 6.

A preferred divalent linking group L is —(—CH2-)n- with n being an integer equal to 1 to 14, more preferably n is equal to 1, 2, 3, 4, 5 or 6.

Preferred monomers according to Formula (II) are given in Table 2, without being limited thereto.

TABLE 2

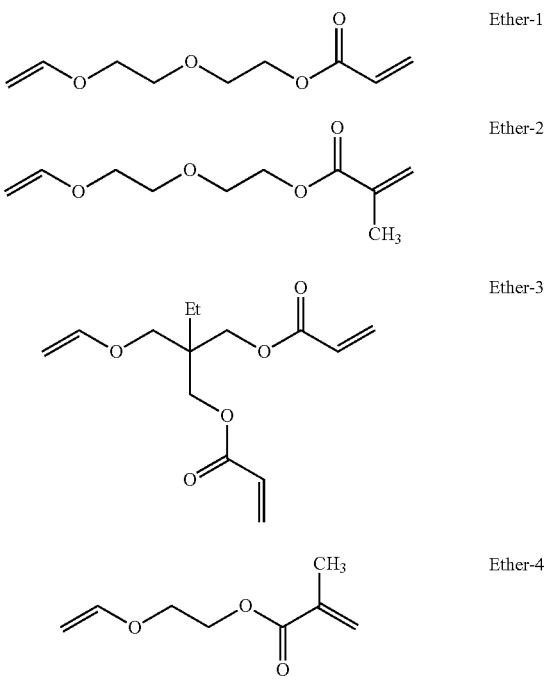

TABLE 2-continued

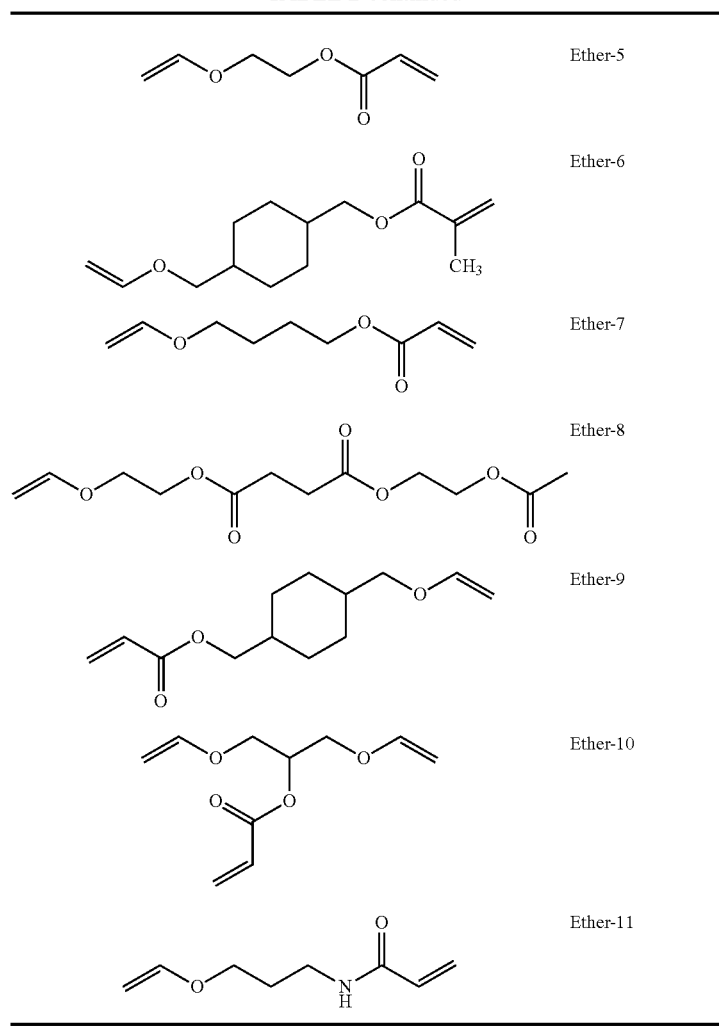

A most preferred monomer according to Formula (II) is 2-(2-vinyloxyethoxy)ethyl acrylate represented by the compound Ether-1 in the Table 2.

Methods of Preparation of Polymerizable Initiators

For preparing the polymerizable photoinitiator, the values for R1, R2, R3, L, A, p and y in the monomer according to Formula (II) are identical to those defined for the polymerizable photoinitiator according to Formula (I).

The polymerizable photoinitiator is prepared according to a method including the steps of:

a) providing a monomer according to Formula (II):

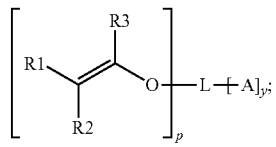

Formula (II)

b) providing a photoinitiator comprising at least one hydroxyl group; and c) catalyzing the reaction between the monomer and the photoinitiator with a catalyst to form a polymerizable photoinitiator according to formula (I):

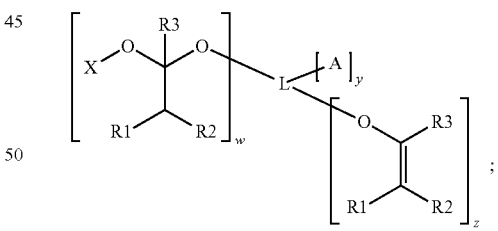

Formula (I)

wherein

R1, R2 and R3 are independently selected from the group consisting of a hydrogen, an optionally substituted alkyl group and an optionally substituted aryl group or R1 and R3 represent the necessary atoms to form a five to eight membered ring;

p, w, y and z are all integers with y being 1 to 6; p being the sum of w and z; p having a value of 1 to 6; w=1 to (p−z) and z=0 to (p−w);

L represents an optionally substituted (p+y)-valent linking group comprising 1 to 14 carbon atoms;

A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, an allyl ester group and a vinyl ester group; and X represents a photoinitiating moiety comprising at least one group capable of initiating a free radical polymerization reaction upon exposure to actinic radiation.

In a most preferred embodiment, the reaction is performed in the absence of an organic solvent. The advantage is that organic solvents need not be removed, which is advantageous both for ecological reasons and when manufacturing radiation curable inkjet inks. These organic solvents tend to evaporate at the nozzles of an inkjet print head during a prolonged non-printing time. When restarting the printer, some nozzles appear to be clogged (=failing nozzles). Latency is the time that a print head can be left uncapped and idle before a failing nozzle appears.

Thus a great advantage of the present method for making the polymerizable photoinitiators is that no organic solvent is required but that the monomer according to Formula (I) can be used as the reaction medium. However, it remains possible in the method for preparing a polymerizable photoinitiator according to a preferred embodiment of the present invention to use one or more organic solvents in the synthesis.

The monomer according to Formula (II) is preferably used not only as reactant but also as reaction medium. The concentration of the monomer according to Formula (II) will be much larger than the concentration of the photoinitiator comprising at least one hydroxyl group. Preferably the molar ratio of the monomer according to Formula (II) over the photoinitiator comprising at least one hydroxyl group is at least 2, more preferably at least 5 and most preferably at least 8 or 10.

If one would use a molar ratio close to 1 and, for example, use a divinylether compound lacking any other polymerizable group as the monomer according to Formula (II), then one would also obtain a substantial amount of difunctional, non-polymerizable photoinitiators. Alternatively, the present method can thus also be used to manufacture difunctional photoinitiators by usage of a molar ratio of about 0.5. Higher multifunctional photoinitiators can be prepared by using a monomer according to Formula (II) having e.g. trivinylether or tetravinylether compounds lacking any other polymerizable group. In such cases, an organic solvent becomes unavoidable for constituting the reaction medium.

It is also possible to add other monomers to the reaction medium, even other monomers according to Formula (II). In the latter, a mixture of different polymerizable photoinitiators may be obtained depending on the concentration of the different monomers according to Formula (II).

After completion of the reaction the radiation curable composition includes at least a polymerizable photoinitiator according to Formula (I), a monomer according to Formula (II) and a catalyst. In a number of cases the catalyst may remain in the radiation curable composition if it does not interfere with the application or the curing of the curable composition. However, most preferably the catalyst is removed. The catalyst could be, for example, polymeric and could lead to an unacceptable viscosity for a UV curable inkjet ink.

The resulting composition including at least one monomer according to Formula (II) capable of free radical polymerization, and a polymerizable photoinitiator, derived from a photoinitiator moiety comprising at least one hydroxyl functional group and the monomer according to Formula (II), can directly be used for the formulation of radiation curable compositions, suitable for food packaging applications.

If required for a specific application, the polymerizable photoinitiator according to Formula (I) or (Ib), can be isolated and purified by any technique known in the prior art such as precipitation, crystallization and optionally chromatography.

The photoinitiator comprising at least one hydroxyl group can be any known photoinitiator having at least one hydroxyl group. It will be readily understood that a photoinitiator having two or more hydroxyl groups is capable of reacting more than once with a monomer according to Formula (II). The photoinitiator comprising at least one hydroxyl group may itself already be a polymerizable photoinitiator. The latter two are both encompassed by the polymerizable photoinitiator according to Formula (I). This is exemplified by the polymerizable photoinitiator INI-13, reproduced here below and cut up in the different parts of Formula (I) with PG representing the extra polymerizable group forming part of the photoinitiating moiety X.

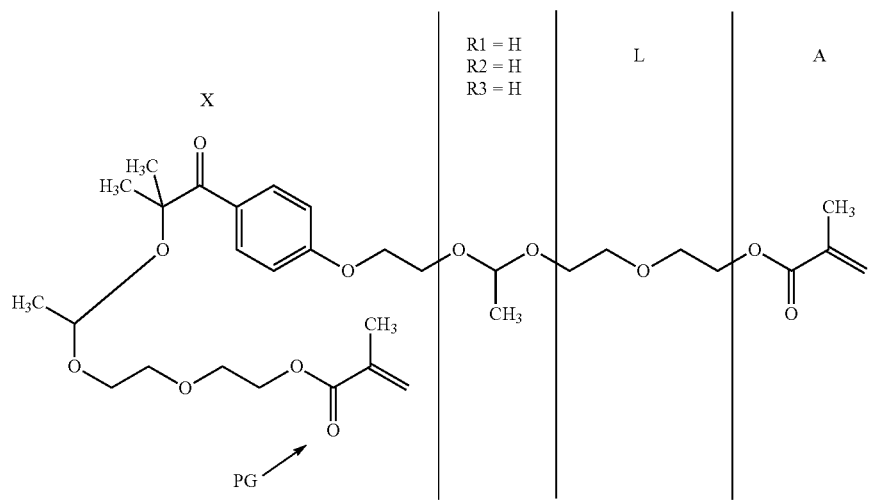

Similar examples include the polymerizable photoinitiators INI-28, INI-29, INI-34 and INI-37.

The photoinitiating moiety X may also be a polymeric group as shown by INI-6 in Table 1 or the star polymeric compound PG shown here below.

Preferred core molecules for a star polymer include trimethylol propane, di-trimethylolpropane, pentaerythritol and di-pentaerythritol.

A photoinitiator lacking at least one hydroxyl group may also first be provided with a hydroxyl group prior to reaction with the monomer according to Formula (II).

PG

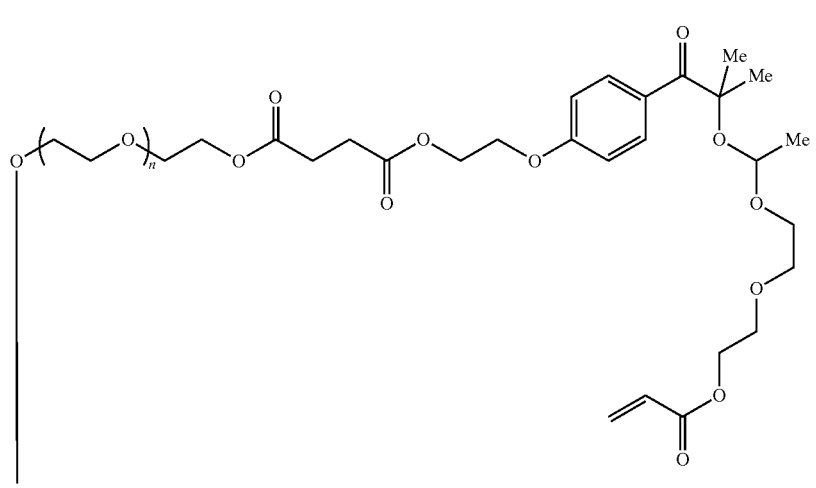

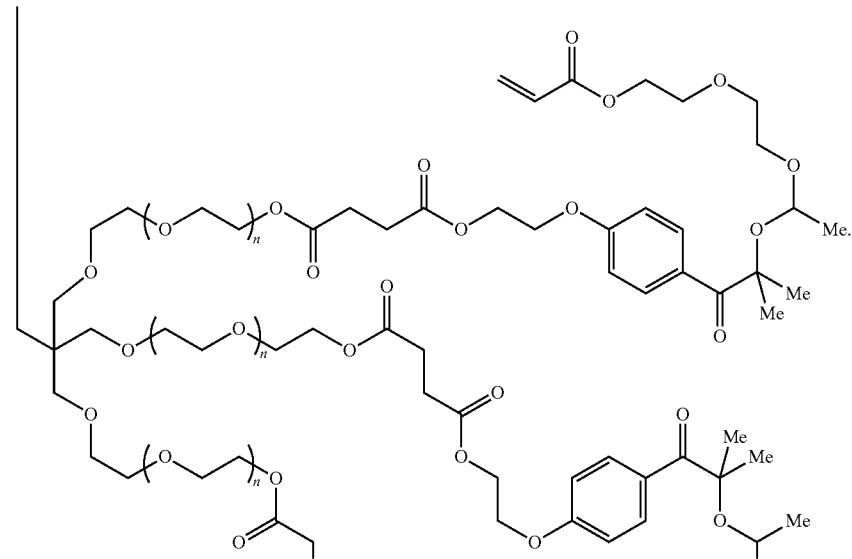

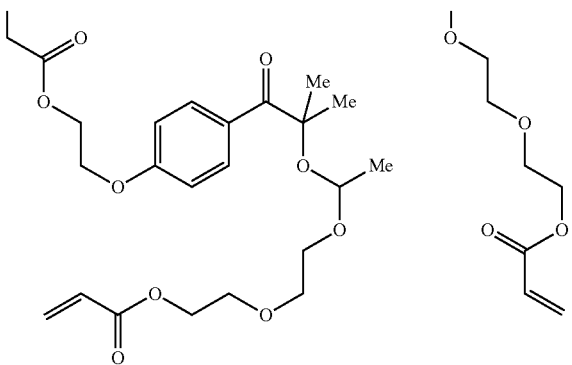

Catalysts

Catalysts used for the preparation of asymmetric acetals by addition of an alcohol to alkenyl-ethers, preferably vinyl ethers, include protic acids with a sufficient low pK, such as hydrochloric acid, phosphoric acid, sulfonic acids, sulfuric acid, and carboxylic acids substituted with electron withdrawing groups such as fluorine and chlorine.

Suitable catalysts include organic salts of sulfonic acids, such as pyridine salts. The use of sulfonic acids as catalyst has been disclosed in numerous documents (e.g. Munro et al., Bioorganic and Medicinal chemistry, 16(3), 1279-1286 (2008); Snowden et al. Helvetica Chimica Acta, 89(12), 3071-3086 (2006), Lucatelli et al., Journal of Organic Chemistry, 67(26), 9468-9470 (2002); Wipf et al., Tetrahedron Letters, 40(28), 5139-5142 (1999)). Typical examples are p.-toluene sulfonic acid, 10-camphor sulfonic acid and methane sulfonic acid.

The use of hydrochloric acid has been disclosed in several documents (e.g. Trofimov et al., Tetrahedron Letters, 49, 3104-3107 (2008)). The use of phosphoric acid has been disclosed by Toshiaki et al. (Tetrahedron Letters, 47, 3251-3255 (2006)).

The use of sulfuric acid has been described by Rappe et al. (Justus Liebigs Annalen der Chemie, 601, 84-111 (1956)).

The use of carboxylic acids, substituted with electron withdrawing substituents has been disclosed in a number of documents (e.g. Rivillo et al., Angewandte Chemie, International Edition, 46(38), 7247-72450 (2007); WO 2007/010483 (Firmenich S. A.); Alvarez de Cienfuego et al., Tetrahedron: asymmetry, 17(2), 1863-1866 (2006); US2005171062 (Allergan Inc.)). Typical examples are trifluoroacetic acid and trichloroacetic acid.

The use organic salts of sulfonic acids has been disclosed in several documents (Lee et al. Bulletin of the Korean Chemical Society, 28(4), 513-514 (2007); Hattori et al., Organic Letters, 10(5), 717-720 (2008); Nakamura et al., Organic Letters, 10(2), 309-312 (2008); Nicolau et al. Journal of the American chemical Society, 129(48), 14850-14851 (2007); Nakamura et al., Tetrahedron, 63(35), 8670-8676 (2007)). A typical example of an organic salt of a sulfonic acid is pyridinium tosylate. Occasionally, also Lewis acids have been reported as catalyst (Alper. H., Synthesis 1972, 81).

Several transition metals have also been shown effective as catalyst for the synthesis of asymmetric acetyls from alkenylethers and alcohols (Maity, G; Synth Commun 1993, 23, 1667; Iqbal, J; Synth Commun 1989, 19, 901; Kantam, M; Synth Commun 1993, 23, 2225; Bhuma, V; Synth Commun 1992, 22, 2941; Ma, S; Tetrahedron Lett 1993, 34, 5269; Molnar, A; Tetrahedron Lett 1996, 37, 8597).

Heterogeneous catalysis has been reported frequently (Bongini, A; Synthesis 1979, 618; Johnston, R; Synthesis 1988, 393; Olah, G; Synthesis 1983, 892; Menger, F; J Org Chem 1981, 46, 5044; Hoyer, S; Synthesis 1986, 655; Upadhya, T; Synth Commun 1996, 26, 4539; Campelo, J; Synth Commun 1994, 24, 1345; Bandgar, B; Synth Commun 1995, 25, 2211; Kumar, P; Synthesis 1993, 1069; Chavez, F; Synth Commun 1992, 22, 159; Patney, H; Synth Commun 1991, 21, 2329; Campelo, J; Synth Commun 1992, 22, 2335).

Acetonyl triphenylphoshonium derivatives have also been reported as catalysts for converting alcohols into asymmetric acetals (Hon et al., Tetrahedron, 57, 5991-6001).

Particularly preferred catalysts are selected from the group consisting of a carboxylic acid substituted with an electron withdrawing group, an organic salt of a sulfonic acid and a heterogeneous catalyst, preferably selected from a salt of crosslinked vinylpyridine containing resins and crosslinked sulfonic acid containing resins.

The most preferred catalysts are selected from the group consisting of trifluoroacetic acid, trichloroacetic acid, pyridinium tosylate, crosslinked poly(vinylpyridine) hydrochloride, poly(vinylpyridinium) tosylate and sulfonic acid substituted ion exchangers.

The acetalysation catalyst can be removed by any technique known in the art. Preferably the catalyst is removed by filtration, neutralization, followed by filtration, neutralization on an ion exchanger or a basic resin and extraction.

Radiation Curable Compositions

The radiation curable composition according to a preferred embodiment of the present invention includes at least the polymerizable photoinitiator according to Formula (I) or (Ib) and most preferably also at least one monomer according to Formula (II).

The radiation curable composition preferably contains 2-(2-vinyloxyethoxy)ethyl acrylate as the monomer according to Formula (II).

The radiation curable composition can be used as a colorless liquid or as a colored liquid, in the latter case it is called a radiation curable ink.

In a preferred embodiment, the radiation curable composition according to the present invention is a radiation curable inkjet composition, more preferably a radiation curable inkjet ink.

The radiation curable compositions and inks can also be advantageously used in offset printing, screen printing, flexographic printing and other printing or coating techniques.

The radiation curable compositions and inks are preferably cured by UV radiation.

In a preferred embodiment, the radiation curable composition according to the present invention is substantially free of organic solvent.

The radiation curable compositions and inks are preferably non-aqueous liquids or inks. The term "non-aqueous" refers to a liquid carrier which should contain no water. However sometimes a small amount, generally less than 5 wt % of water based on the total weight of the composition or ink, can be present. This water was not intentionally added but came into the formulation via other components as a contamination, such as for example polar organic solvents. Higher amounts of water than 5 wt % tend to make the non-aqueous liquids and inks instable, preferably the water content is less than 1 wt % based on the total weight of radiation curable composition or ink and most preferably no water at all is present.

The radiation curable compositions and inks preferably do not contain an evaporable component such as an organic solvent. But sometimes it can be advantageous to incorporate a small amount of an organic solvent to improve adhesion to the surface of a substrate after UV-curing. In this case, the added solvent can be any amount in the range that does not cause problems of solvent resistance and VOC, and preferably 0.1-10.0 wt %, and particularly preferably 0.1-5.0 wt %, each based on the total weight of the curable composition or ink.

The radiation curable compositions and inks are preferably part of an ink set, more preferably an inkjet ink set, comprising at least one ink containing one or more colorants, preferably one or more color pigments. The curable ink set preferably comprises at least one yellow curable ink (Y), at least one cyan curable ink (C) and at least one magenta curable ink (M) and preferably also at least one black curable ink (K). The curable CMYK-ink set may also be extended with extra inks such as red, green, blue, and/or orange to further enlarge the color gamut of the image. The CMYK-ink set may also be extended by the combination of full density and light density inks of both color inks and/or black inks to improve the image quality by lowered graininess.

The pigmented radiation curable ink preferably contains a dispersant, more preferably a polymeric dispersant, for dispersing the pigment. The pigmented curable ink may contain a dispersion synergist to improve the dispersion quality and stability of the ink. Preferably, at least the magenta ink contains a dispersion synergist. A mixture of dispersion synergists may be used to further improve dispersion stability.

The viscosity of the curable liquid and ink is preferably smaller than 100 mPa·s at 30° C. and at a shear rate of 100 s$^{-1}$. The viscosity of the radiation curable inkjet inks and liquids is preferably smaller than 50 mPa·s, more preferably lower than 30 mPa·s, and most preferably between 2 and 15 mPa·s at a shear rate of 100 s$^{-1}$ and a jetting temperature between 10 and 70° C.

The surface tension of the curable liquid and ink is preferably in the range of about 20 mN/m to about 70 mN/m at 25° C., more preferably in the range of about 22 mN/m to about 40 mN/m at 25° C.

The curable composition or ink may further also contain at least one inhibitor for improving the thermal stability of composition or ink.

The curable composition or ink may further also contain at least one surfactant for obtaining good spreading characteristics on a substrate.

Co-Initiators

The radiation curable composition according to a preferred embodiment of the present invention may contain one or more co-initiators. A preferred amount of the co-initiator is 1 to 30 wt %, more preferably 2 to 20 wt %, and most preferably 5 to 10 wt % of the total weight of the radiation curable composition.

For safety reasons, in particular for food packaging applications, the radiation curable composition according to a preferred embodiment of the present invention contains at least one so-called diffusion hindered co-initiator. A diffusion hindered co-initiator is a co-initiator which exhibits a much lower mobility in a cured layer of the radiation curable composition or ink than a monofunctional, non-polymerizable co-initiator, such as a dialkylaminobenzoate. Several methods can be used to lower the mobility of the co-initiator. One way is to increase the molecular weight of the co-initiator so that the diffusion speed is reduced, e.g. multifunctional co-initiators or polymeric co-initiators. Another way is to increase its reactivity so that it is built into the polymerizing network, e.g. multifunctional co-initiators and polymerizable co-initiators.

The diffusion hindered co-initiator is preferably selected from the group consisting of non-polymeric di- or multifunctional co-initiators, oligomeric or polymeric co-initiators and polymerizable co-initiators. Non-polymeric di- or multifunctional co-initiators usually have a molecular weight between 300 and 900 Dalton. Monofunctional co-initiators with a molecular weight in that range are not diffusion hindered co-initiators.

In a preferred embodiment of the radiation curable composition according to a preferred embodiment of the present invention, the at least one co-initiator is a diffusion hindered dialkylamino substituted aromatic compound selected from the group consisting of an oligomeric or polymeric dialkylamino substituted aromatic compound, a multifunctional dialkylamino substituted aromatic compound and a dialkylamino substituted aromatic compound comprising at least one polymerizable ethylenically unsaturated group. A dialkylamino substituted aromatic compound comprising at least one polymerizable ethylenically unsaturated group is particularly preferred.

In a more preferred embodiment the dialkylamino substituted aromatic compound comprising at least one polymerizable ethylenically unsaturated group is a co-initiator according to Formula (C-I):

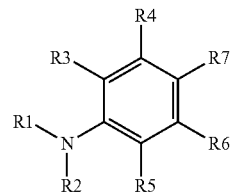

Formula (C-I)

wherein,

R1 and R2 are independently selected from the group consisting of an alkyl group, an alkenyl group, an alkynyl group, an aralkyl group, an alkaryl group, an aryl group and a heteroaryl group;

R3 to R6 are independently selected from the group consisting of hydrogen, an alkyl group, an alkenyl group, an alkynyl group, an acyl group, a thioalkyl group, an alkoxy group, a halogen, an aralkyl group, an alkaryl group, an aryl group and a heteroaryl group;

R7 is selected from the group consisting of hydrogen, an aldehyde group, a ketone group, an ester group, an amide group, an acyl group, a thioalkyl group, an alkoxy group, a halogen, a nitrile group, a sulphonate group, a sulphonamide group, an alkyl group, an alkenyl group, an alkynyl group, an aralkyl group, an alkaryl group, an aryl group and a heteroaryl group;

R1 and R2, R1 and R3, R2 and R5, R3 and R4, R4 and R7, R5 and R6, and R6 and R7 may represent the necessary atoms to form a 5- to 8-membered ring; and with the proviso that the aromatic amine has at least one α-hydrogen; and at least one of R1 to R7 comprises a polymerizable ethylenically unsaturated functional group selected from the group consisting of acrylate, substituted acrylate, methacrylate, styrene, acrylamide, methacrylamide, allyl ester, allyl ether, vinyl ester, vinyl ether, fumarate, maleate, maleimide and vinyl nitrile. In the polymerizable co-initiator, preferably R7 represents an electron withdrawing group selected from the group consisting of an aldehyde, a ketone, an ester and an amide, and more preferably R3, R4, R5 and R6 all represent hydrogen.

The alkyl groups, alkenyl groups, alkynyl groups, aralkyl groups, alkaryl groups, aryl groups and heteroaryl groups used for R1 to R7 can be substituted or unsubstituted groups, i.e. a substituted or unsubstituted alkyl group, a substituted or unsubstituted alkenyl group, a substituted or unsubstituted alkynyl group, a substituted or unsubstituted aralkyl group, a substituted or unsubstituted alkaryl group and a substituted or unsubstituted (hetero)aryl group may be used.

In a preferred embodiment, the polymerizable co-initiator corresponds to Formula (C-II):

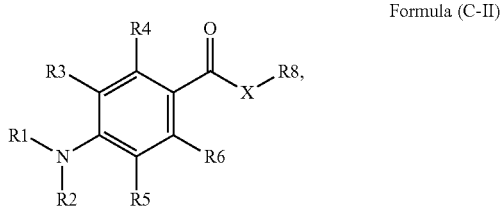

Formula (C-II)

wherein,

R1 to R6 have the same meaning as defined for Formula (C-I);

X is selected from the group consisting of O, S and NR9;

R8 and R9 are independently selected from the group consisting of hydrogen, an alkyl group, an alkenyl group, an alkynyl group, an aralkyl group, an alkaryl group, an aryl group and a heteroaryl group;

R1 and R2, R1 and R3, R2 and R5, R3 and R4, R5 and R6, R4 and R8, R6 and R8, and R8 and R9 may represent the necessary atoms to form a 5- to 8-membered ring; and at least one of R1 to R6 and R8 comprises a polymerizable ethylenically unsaturated functional group selected from the group consisting of acrylate, substituted acrylate, methacrylate, styrene, acrylamide, methacrylamide, allyl ester, allyl ether, vinyl ester, vinyl ether, fumarate, maleate, maleimide and vinyl nitrile. In the polymerizable co-initiator, preferably R3, R4, R5 and R6 all represent hydrogen.

In one preferred embodiment of the polymerizable co-initiator having Formula (C-II), R1 represents methyl or ethyl and R2 comprises a polymerizable ethylenically unsaturated functional group selected from the group consisting of acrylate, substituted acrylate, methacrylate, styrene, acrylamide, methacrylamide, allyl ester, allyl ether, vinyl ester, vinyl ether, fumarate, maleate, maleimide and vinyl nitrile; and more preferably also R3, R4, R5 and R6 all represent hydrogen.

In another preferred embodiment of the polymerizable co-initiator having Formula (C-I), R1 and R2 independently represent methyl or ethyl and R8 comprises a polymerizable ethylenically unsaturated functional group selected from the group consisting of acrylate, substituted acrylate, methacrylate, styrene, acrylamide, methacrylamide, allyl ester, allyl ether, vinyl ester, vinyl ether, fumarate, maleate, maleimide and vinyl nitrile; and more preferably also R3, R4, R5 and R6 all represent hydrogen.

In a more preferred embodiment, the polymerizable co-initiator corresponds to Formula (C-III):

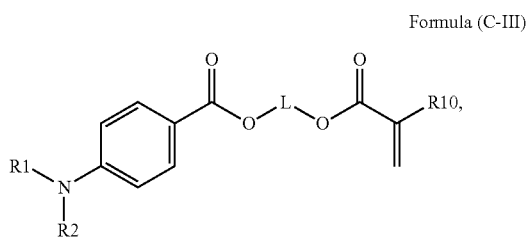

Formula (C-III)

wherein,

R1 and R2 are independently selected from the group consisting of methyl, ethyl, propyl and butyl;

L represents a divalent linking group comprising at least one carbon atom; and

R10 represents hydrogen, methyl, ethyl, propyl or butyl.

In a preferred embodiment of the polymerizable co-initiator corresponding to Formula (C-III), the divalent linking group L comprises 1 to 30 carbon atoms, more preferably 2 to 10 carbon atoms and most preferably 3 to 6 atoms.

The polymerizable co-initiator may contain two, three or more polymerizable ethylenically unsaturated functional groups independently selected from the group consisting of acrylate, substituted acrylate, methacrylate, styrene, acrylamide, methacrylamide, allyl ester, allyl ether, vinyl ester, vinyl ether, fumarate, maleate, maleimide and vinyl nitrile.

Monomers and Oligomers

The monomers and oligomers used in the radiation curable compositions and inks, especially for food packaging applications, are preferably purified compounds having no or almost no impurities, more particularly no toxic or carcinogenic impurities. The impurities are usually derivative compounds obtained during synthesis of the polymerizable compound. Sometimes, however, some compounds may be added deliberately to pure polymerizable compounds in harmless amounts, for example, polymerization inhibitors or stabilizers.

Any monomer or oligomer capable of free radical polymerization may be used as polymerizable compound. A combination of monomers, oligomers and/or prepolymers may also be used. The monomers, oligomers and/or prepolymers may possess different degrees of functionality, and a mixture including combinations of mono-, di-, tri- and higher functionality monomers, oligomers and/or prepolymers may be used. The viscosity of the radiation curable compositions and inks can be adjusted by varying the ratio between the monomers and oligomers.

Particularly preferred monomers and oligomers are those listed in [0106] to [0115] in EP 1911814 A (AGFA GRAPHICS) incorporated herein as a specific reference.

A preferred class of monomers and oligomers are vinyl ether acrylates such as those described in U.S. Pat. No. 6,310,115 (AGFA), incorporated herein by reference. Particularly preferred compounds are 2-(2-vinyloxyethoxy)ethyl (meth)acrylate, most preferably the compound is 2-(2-vinyloxyethoxy)ethyl acrylate.

Inhibitors

The radiation curable compositions and inks may contain a polymerization inhibitor. Suitable polymerization inhibitors include phenol type antioxidants, hindered amine light stabilizers, phosphor type antioxidants, hydroquinone monomethyl ether commonly used in (meth)acrylate monomers, and hydroquinone, t-butylcatechol, pyrogallol, 2,6-di-tert.butyl-4-methylphenol may also be used.

Suitable commercial inhibitors are, for example, SUMILIZER™ GA-80, SUMILIZER™ GM and SUMILIZER™ GS produced by Sumitomo Chemical Co. Ltd.; GENORAD™16, GENORAD™18 and GENORAD™ 20 from Rahn AG; IRGASTAB™ UV10 and IRGASTAB™ UV22, TINUVIN™ 460 and CGS20 from Ciba Specialty Chemicals; FLOORSTAB™ UV range (UV-1, UV-2, UV-5 and UV-8) from Kromachem Ltd, ADDITOL™ S range (S100, S110, S120 and S130) from Cytec Surface Specialties.

The inhibitor is preferably a polymerizable inhibitor.

Since excessive addition of these polymerization inhibitors may lower the curing speed, it is preferred that the amount capable of preventing polymerization is determined prior to blending. The amount of a polymerization inhibitor is preferably lower than 5 wt %, more preferably lower than 3 wt % of the total ink or liquid.

Surfactants

The radiation curable compositions and inks may contain a surfactant. The surfactant(s) can be anionic, cationic, non-ionic, or zwitter-ionic and are usually added in a total quantity less than 10 wt % based on the total weight of the radiation curable compositions or ink and particularly in a total less than 5 wt % based on the total weight of the radiation curable composition or ink.

Suitable surfactants include those disclosed in paragraphs [0283] to [0291] of WO 2008/074548 (AGFA GRAPHICS) incorporated herein as a specific reference.

Colorants

Colorants used in the radiation curable inks may be dyes, pigments or a combination thereof. Organic and/or inorganic pigments may be used. The colorant is preferably a pigment or a polymeric dye, most preferably a pigment.

The pigments may be black, white, cyan, magenta, yellow, red, orange, violet, blue, green, brown, mixtures thereof, and the like. This color pigment may be chosen from those disclosed by HERBST, Willy, et al. Industrial Organic Pigments, Production, Properties, Applications. 3rd edition. Wiley-VCH, 2004. ISBN 3527305769.

Suitable pigments are disclosed in paragraphs [0128] to [0138] of WO 2008/074548 (AGFA GRAPHICS).

Suitable pigments include mixed crystals of the above particular preferred pigments. Mixed crystals are also referred to as solid solutions. For example, under certain conditions different quinacridones mix with each other to form solid solutions, which are quite different from both physical mixtures of the compounds and from the compounds themselves. In a solid solution, the molecules of the components enter into the same crystal lattice, usually, but not always, that of one of the components. The x-ray diffraction pattern of the resulting crystalline solid is characteristic of that solid and can be clearly differentiated from the pattern of a physical mixture of the same components in the same proportion. In such physical mixtures, the x-ray pattern of each of the components can be distinguished, and the disappearance of many of these lines is one of the criteria of the formation of solid solutions. A commercially available example is CINQUASIA™ Magenta RT-355-D from Ciba Specialty Chemicals.

Also mixtures of pigments may be used in the radiation curable inks. For some inkjet applications, a neutral black inkjet ink is preferred and can be obtained, for example, by mixing a black pigment and a cyan pigment into the ink. The inkjet application may also require one or more spot colors, for example for packaging inkjet printing or textile inkjet printing. Silver and gold are often desired colors for inkjet poster printing and point-of-sales displays.

Non-organic pigments may be used in the color inkjet inks. Particular preferred pigments are C.I. Pigment Metal 1, 2 and 3. Illustrative examples of the inorganic pigments include red iron oxide (III), cadmium red, ultramarine blue, prussian blue, chromium oxide green, cobalt green, amber, titanium black and synthetic iron black.

Pigment particles in inkjet inks should be sufficiently small to permit free flow of the ink through the inkjet-printing device, especially at the ejecting nozzles. It is also desirable to use small particles for maximum color strength and to slow down sedimentation.

The numeric average pigment particle size is preferably between 0.050 and 1 μm, more preferably between 0.070 and 0.300 μm and particularly preferably between 0.080 and 0.200 μm. Most preferably, the numeric average pigment particle size is no larger than 0.150 μm. An average particle size smaller than 0.050 μm is less desirable for decreased light-fastness, but mainly also because very small pigment particles or individual pigment molecules thereof may still be extracted in food packaging applications. The average particle size of pigment particles is determined with a Brookhaven Instruments Particle Sizer BI90plus based upon the principle of dynamic light scattering. The ink is diluted with ethyl acetate to a pigment concentration of 0.002 wt %. The measurement settings of the BI90plus are: 5 runs at 23° C., angle of 90°, wavelength of 635 nm and graphics=correction function.

However for a white radiation curable ink, the numeric average particle diameter of the white pigment is preferably from 50 to 500 nm, more preferably from 150 to 400 nm, and most preferably from 200 to 350 nm. Sufficient hiding power cannot be obtained when the average diameter is less than 50 nm, and the storage ability and the jet-out suitability of the ink tend to be degraded when the average diameter exceeds 500 nm. The determination of the numeric average particle diameter is best performed by photon correlation spectroscopy at a wavelength of 633 nm with a 4 mW HeNe laser on a diluted sample of the pigmented inkjet ink. A suitable particle size analyzer used was a MALVERN™ nano-S available from Goffin-Meyvis. A sample can be, for example, be prepared by addition of one drop of ink to a cuvet containing 1.5 mL ethyl acetate and mixed until a homogenous sample was obtained. The measured particle size is the average value of 3 consecutive measurements consisting of 6 runs of 20 seconds.

Suitable white pigments are given by Table 2 in [0116] of WO 2008/074548 (AGFA GRAPHICS). The white pigment is preferably a pigment with a refractive index greater than 1.60. The white pigments may be employed singly or in combination. Preferably titanium dioxide is used as pigment with a refractive index greater than 1.60. Suitable titanium dioxide pigments are those disclosed in [0117] and in [0118] of WO 2008/074548 (AGFA GRAPHICS).

The pigments are present in the range of 0.01 to 10% by weight, preferably in the range of 0.1 to 5% by weight, each based on the total weight of radiation curable ink. For white radiation curable inks, the white pigment is preferably present in an amount of 3% to 30% by weight of the ink composition, and more preferably 5% to 25%. An amount of less than 3% by weight cannot achieve sufficient covering power and usually exhibits very poor storage stability and ejection property.

Generally pigments are stabilized in the dispersion medium by dispersing agents, such as polymeric dispersants. However, the surface of the pigments can be modified to obtain so-called "self-dispersible" or "self-dispersing" pigments, i.e. pigments that are dispersible in the dispersion medium without dispersants.

Dispersants

The dispersant is preferably a polymeric dispersant. Typical polymeric dispersants are copolymers of two monomers but may contain three, four, five or even more monomers. The properties of polymeric dispersants depend on both the nature of the monomers and their distribution in the polymer. Suitable copolymeric dispersants have the following polymer compositions:

statistically polymerized monomers (e.g. monomers A and B polymerized into ABBAABAB);
  alternating polymerized monomers (e.g. monomers A and B polymerized into ABABABAB);
  gradient (tapered) polymerized monomers (e.g. monomers A and B polymerized into AAABAABBABBB);
  block copolymers (e.g. monomers A and B polymerized into AAAAABBBBBB) wherein the block length of each of the blocks (2, 3, 4, 5 or even more) is important for the dispersion capability of the polymeric dispersant;

graft copolymers (graft copolymers consist of a polymeric backbone with polymeric side chains attached to the backbone); and mixed forms of these polymers, e.g. blocky gradient copolymers.

Suitable polymeric dispersants are listed in the section on "Dispersants", more specifically [0064] to [0070] and [0074] to [0077], in EP 1911814 A (AGFA GRAPHICS) incorporated herein as a specific reference.

The polymeric dispersant has preferably a number average molecular weight Mn between 500 and 30,000, more preferably between 1,500 and 10,000.

The polymeric dispersant has preferably a weight average molecular weight Mw smaller than 100,000, more preferably smaller than 50,000 and most preferably smaller than 30,000.

The polymeric dispersant has preferably a polydispersity PD smaller than 2, more preferably smaller than 1.75 and most preferably smaller than 1.5.

Commercial examples of polymeric dispersants are the following:

DISPERBYK™ dispersants available from BYK CHEMIE GMBH;
SOLSPERSE™ dispersants available from NOVEON;
TEGO™ DISPERS™ dispersants from DEGUSSA;
EDAPLAN™ dispersants from MÜNZING CHEMIE;
ETHACRYL™ dispersants from LYONDELL;
GANEX™ dispersants from ISP;
DISPEX™ and EFKA™ dispersants from CIBA SPECIALTY CHEMICALS INC;
DISPONER™ dispersants from DEUCHEM; and
JONCRYL™ dispersants from JOHNSON POLYMER.

Particularly preferred polymeric dispersants include SOLSPERSE™ dispersants from NOVEON, EFKA™ dispersants from CIBA SPECIALTY CHEMICALS INC and DISPERBYK™ dispersants from BYK CHEMIE GMBH. Particularly preferred dispersants are SOLSPERSE™ 32000, 35000 and 39000 dispersants from NOVEON.

The polymeric dispersant is preferably used in an amount of 2 to 600 wt %, more preferably 5 to 200 wt % based on the weight of the pigment.

Dispersion Synergists

A dispersion synergist usually consists of an anionic part and a cationic part. The anionic part of the dispersion synergist exhibiting a certain molecular similarity with the color pigment and the cationic part of the dispersion synergist consists of one or more protons and/or cations to compensate the charge of the anionic part of the dispersion synergist.

The synergist is preferably added in a smaller amount than the polymeric dispersant(s). The ratio of polymeric dispersant/dispersion synergist depends upon the pigment and should be determined experimentally. Typically the ratio wt % polymeric dispersant/wt % dispersion synergist is selected between 2:1 to 100:1, preferably between 2:1 and 20:1.

Suitable dispersion synergists that are commercially available include SOLSPERSE™ 5000 and SOLSPERSE™ 22000 from NOVEON.

Particular preferred pigments for the magenta ink used are a diketopyrrolo-pyrrole pigment or a quinacridone pigment. Suitable dispersion synergists include those disclosed in EP 1790698 A (AGFA GRAPHICS), EP 1790696 A (AGFA GRAPHICS), WO 2007/060255 (AGFA GRAPHICS) and EP 1790695 A (AGFA GRAPHICS).

In dispersing C.I. Pigment Blue 15:3, the use of a sulfonated Cu-phthalocyanine dispersion synergist, e.g. SOLSPERSE™ 5000 from NOVEON is preferred. Suitable dispersion synergists for yellow inkjet inks include those disclosed in EP 1790697 A (AGFA GRAPHICS).

Preparation of Radiation Curable Inks

The average particle size and distribution is an important feature for inkjet inks. The ink may be prepared by precipitating or milling the pigment in the dispersion medium in the presence of the dispersant.

Mixing apparatuses may include a pressure kneader, an open kneader, a planetary mixer, a dissolver, and a Dalton Universal Mixer. Suitable milling and dispersion apparatuses are a ball mill, a pearl mill, a colloid mill, a high-speed disperser, double rollers, a bead mill, a paint conditioner, and triple rollers. The dispersions may also be prepared using ultrasonic energy.

Many different types of materials may be used as milling media, such as glasses, ceramics, metals, and plastics. In a preferred embodiment, the grinding media can comprise particles, preferably substantially spherical in shape, e.g. beads consisting essentially of a polymeric resin or yttrium stabilized zirconium oxide beads.

In the process of mixing, milling and dispersion, each process is performed with cooling to prevent build up of heat, and for radiation curable inks as much as possible under light conditions in which actinic radiation has been substantially excluded.

The ink may contain more than one pigment, the ink may be prepared using separate dispersions for each pigment, or alternatively several pigments may be mixed and co-milled in preparing the dispersion.

The dispersion process can be carried out in a continuous, batch or semi-batch mode.

The preferred amounts and ratios of the ingredients of the mill grind will vary widely depending upon the specific materials and the intended applications. The contents of the milling mixture comprise the mill grind and the milling media. The mill grind comprises pigment, polymeric dispersant and a liquid carrier. For inkjet inks, the pigment is usually present in the mill grind at 1 to 50 wt %, excluding the milling media. The weight ratio of pigment over polymeric dispersant is 20:1 to 1:2.

The milling time can vary widely and depends upon the pigment, selected mechanical means and residence conditions, the initial and desired final particle size, etc. In a preferred embodiment of the present invention pigment dispersions with an average particle size of less than 100 nm may be prepared.

After milling is completed, the milling media is separated from the milled particulate product (in either a dry or liquid dispersion form) using conventional separation techniques, such as by filtration, sieving through a mesh screen, and the like. Often the sieve is built into the mill, e.g. for a bead mill. The milled pigment concentrate is preferably separated from the milling media by filtration.

In general it is desirable to make the inks in the form of a concentrated mill grind, which is subsequently diluted to the appropriate concentration for use in the printing system. This technique permits preparation of a greater quantity of pigmented ink from the equipment. By dilution, the ink is adjusted to the desired viscosity, surface tension, color, hue, saturation density, and print area coverage for the particular application.

Inkjet Printing Device

Curable compositions and inks according to a preferred embodiment of the present invention may be jetted by one or more print heads ejecting small droplets of ink in a controlled manner through nozzles onto an ink-receiver surface, which is moving relative to the print head(s).

A preferred print head for the inkjet printing system is a piezoelectric head. Piezoelectric inkjet printing is based on the movement of a piezoelectric ceramic transducer when a voltage is applied thereto. The application of a voltage changes the shape of the piezoelectric ceramic transducer in the print head creating a void, which is then filled with ink. When the voltage is again removed, the ceramic expands to its original shape, ejecting a drop of ink from the print head. However the inkjet printing method according to the present invention is not restricted to piezoelectric inkjet printing. Other inkjet print heads can be used and include various types, such as a continuous type and thermal, electrostatic and acoustic drop on demand type.

At high printing speeds, the inks must be ejected readily from the print heads, which puts a number of constraints on the physical properties of the ink, e.g. a low viscosity at the jetting temperature, which may vary from 25° C. to 110° C., a surface energy such that the print head nozzle can form the necessary small droplets, a homogenous ink capable of rapid conversion to a dry printed area, . . . .

The inkjet print head normally scans back and forth in a transversal direction across the moving ink-receiver surface. Often the inkjet print head does not print on the way back. Bi-directional printing is preferred for obtaining a high areal throughput. Another preferred printing method is by a "single pass printing process", which can be performed by using page wide inkjet print heads or multiple staggered inkjet print heads which cover the entire width of the ink-receiver surface. In a single pass printing process the inkjet print heads usually remain stationary and the ink-receiver surface is transported under the inkjet print heads.

Curing Device

Curable compositions and inks according to a preferred embodiment of the present invention can be cured by exposing them to actinic radiation, preferably by ultraviolet radiation.

In inkjet printing, the curing device may be arranged in combination with the print head of the inkjet printer, traveling therewith so that the curable composition is exposed to curing radiation very shortly after been jetted.

In such an arrangement it can be difficult to provide a small enough radiation source connected to and traveling with the print head. Therefore, a static fixed radiation source may be employed, e.g. a source of curing UV-light, connected to the radiation source by a flexible radiation conductive device such as a fiber optic bundle or an internally reflective flexible tube.

Alternatively, the actinic radiation may be supplied from a fixed source to the radiation head by an arrangement of mirrors including a mirror upon the radiation head.

The source of radiation arranged not to move with the print head, may also be an elongated radiation source extending transversely across the ink-receiver surface to be cured and adjacent the transverse path of the print head so that the subsequent rows of images formed by the print head are passed, stepwise or continually, beneath that radiation source.

Any ultraviolet light source, as long as part of the emitted light can be absorbed by the photo-initiator or photo-initiator system, may be employed as a radiation source, such as, a high or low pressure mercury lamp, a cold cathode tube, a black light, an ultraviolet LED, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing.

UV radiation is generally classed as UV-A, UV-B, and UV-C as follows:

UV-A: 400 nm to 320 nm
UV-B: 320 nm to 290 nm
UV-C: 290 nm to 100 nm.

Furthermore, it is possible to cure the image using, consecutively or simultaneously, two light sources of differing wavelength or illuminance. For example, the first UV-source can be selected to be rich in UV-C, in particular in the range of 260 nm-200 nm. The second UV-source can then be rich in UV-A, e.g. a gallium-doped lamp, or a different lamp high in both UV-A and UV-B. The use of two UV-sources has been found to have advantages e.g. a fast curing speed and a high curing degree.

For facilitating curing, the inkjet printer often includes one or more oxygen depletion units. The oxygen depletion units place a blanket of nitrogen or other relatively inert gas (e.g. $CO_2$), with adjustable position and adjustable inert gas concentration, in order to reduce the oxygen concentration in the curing environment. Residual oxygen levels are usually maintained as low as 200 ppm, but are generally in the range of 200 ppm to 1200 ppm.

EXAMPLES

Materials

All materials used in the following examples were readily available from Aldrich Chemical Co. (Belgium) unless otherwise specified.

The water used was deionized water.

TEGO™ Rad 2100 is a silicone polyether acrylate surfactant available from DEGUSSA.

PET100 is a 100 µm unsubbed PET substrate with on the backside an antiblocking layer with antistatic properties available from AGFA-GEVAERT as P100C PLAIN/ABAS.

BHT is an abbreviation for 2,6-di-tert.butyl-4-methylphenol, available from ALDRICH CHEMICAL CO.

LEWATIT™ M600 MB from BAYER

Ether-1 is 2-(2-vinyloxyethoxy)ethyl acrylate, a difunctional monomer available from Nippon Shokubai, Japan.

Ether-2 is 2-(2-vinyloxyethoxy)ethyl methacrylate, a difunctional monomer available from Nippon Shokubai, Japan.

Ether-4 is vinyloxyethylmethacrylate available from Nippon Shokubai, Japan.

Ether-5 is vinyloxyethylacrylate available from Nippon Shokubai, Japan.

M600 is dipentaerithritol hexaacrylate and an abbreviation for MIRAMER™ M600, available from Rahn AG.

SR339C is SARTOMER™ SR339C available from SARTOMER:

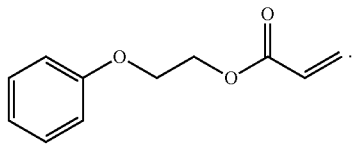

SR9003 is SARTOMER™ SR9003 available from SARTOMER:

SR8335 is SARTOMER™ 8335 available from SARTOMER:

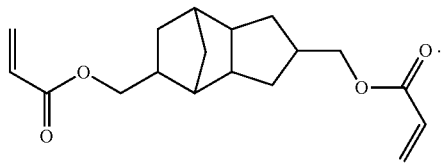 [SMILES: C=CC(=O)OCC1CC2C3CC(COC(=O)C=C)C(C3)C2C1]

SR508 is SARTOMER™ SR508 available from SARTOMER:

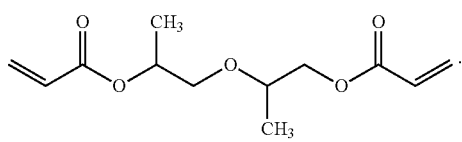 [SMILES: C=CC(=O)OCC(C)OCC(C)OC(=O)C=C]

Type II is a polymerizable thioxanthone derivative according to the following structure:

Type II

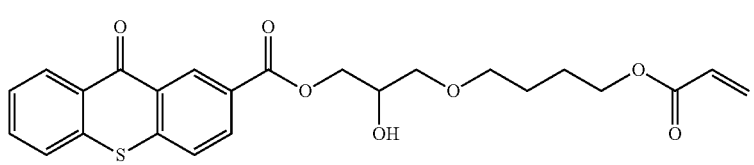

and can be prepared as follows:

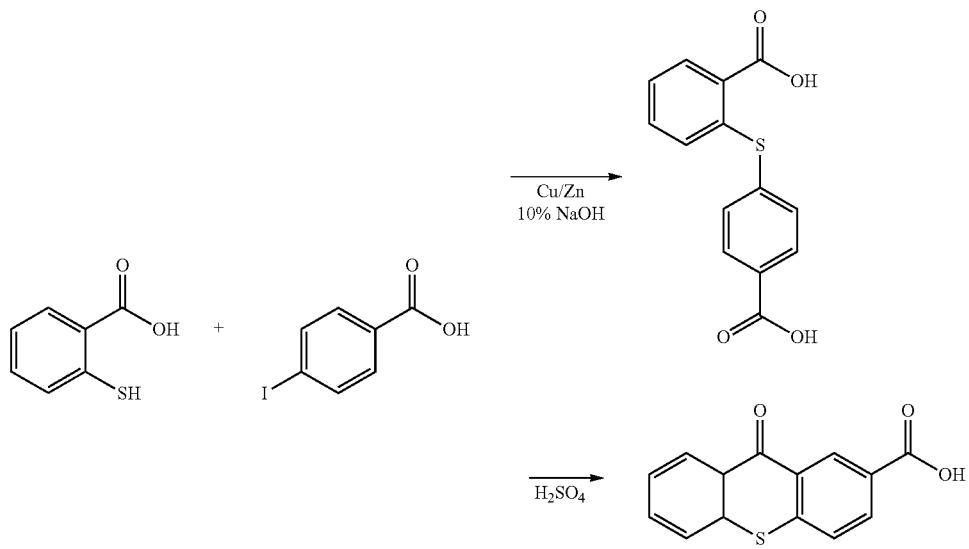 [SMILES: O=C(O)c1ccccc1S ; O=C(O)c1ccc(I)cc1 ; O=C(O)c1ccc(Sc2ccccc2C(=O)O)cc1 ; "H2SO4" ; O=C(O)c1ccc2c(c1)C(=O)C1C=CC=CC1S2]

diphenylsulfide-2,4'-dicarboxylic acid:
31.08 g (202 mmol) thiosalicylic acid and 50 g (202 mmol) 4-iodo-benzoic acid were added to 410 mL of 10% NaOH. 12.3 g copper powder and 2.04 g zinc powder were added and the mixture was refluxed for 6 hours, while vigorously stirring. The foaming was difficult to control. The reaction mixture was allowed to cool down to room temperature. The copper and zinc powder were removed by filtration. The reaction mixture was diluted with 800 mL water and neutralized with 600 mL 2N HCl. The precipitated diphenylsulfide-2,4'-dicarboxylic acid was isolated by filtration washed three times with water and dried. 55 g of diphenylsulfide-2,4'-dicarboxylic acid was isolated. (m.p. 235-237° C.) 9-oxo-9H-thioxanthene-2-carboxylic acid 52.74 (192 mmol) diphenylsulfide-2,4'-dicarboxylic acid was dissolved in 1 L concentrated sulfuric acid and the reaction was allowed to continue for 24 hours at room temperature. The reaction mixture was added slowly to 12 L boiling water. The mixture was kept at 100° C. for an additional hour. The mixture was allowed to cool down to room temperature. The crude 9-oxo-9H-thioxanthene-2-carboxylic acid precipitated from the mixture, was isolated by filtration, washed three times with water and once with ethanol and dried. 41.76 g of the crude 9-oxo-9H-thioxanthene-2-carboxylic acid was dissolved in 417 mL 2N NaOH, stirred for 30 minutes at room temperature and slowly acidified with 600 mL 2N HCl. The mixture was stirred for 30 minutes and the precipitated 9-oxo-9H-thioxanthene-2-carboxylic acid was isolated by filtration, washed twice with water and twice with ethanol and dried. 31.5 g (64%) 9-oxo-9H-thioxanthene-2-carboxylic acid was isolated (m.p.: 310-316° C.).

A reaction mixture containing 9-oxo-9H-thioxanthene-2-carboxylic acid (2.0 g, 7.8 mmol), acetonitrile (30 mL), dimethylacetamide (20 mL), tetrabutylammonium bromide (0.3 g, 0.78 mmol) and 2,6-di-tert-butyl-4-methylphenol (0.02 g, 0.0634 mmol) was heated to reflux. At this temperature 4-hydroxybutylacrylate glycidylether (1.3 g, 6.34 mmol) was added and the mixture was allowed to stir at reflux temperature for 24 hours.

The mixture was cooled to room temperature and filtered to remove the residual, undissolved 9-oxo-9H-thioxanthene-2-carboxylic acid.

The filtrate was evaporated under reduced pressure.

The residual oil was dissolved in methyl-tert-butylether (100 mL) and extracted with a mixture of an aqueous solution of sodium hydroxide (1N) and distilled water (1/4).

The organic layer was separated, dried on MgSO$_4$, filtered and evaporated to provide 2.5 g of a brown oil.

COINI-1 is a polymerizable coinitiator according to the following structure:

and can be prepared as follows:

4.2 g (215 mmol) of 85% KOH was dissolved in 100 mL ethanol. The temperature rose to 30° C. 30 g (178 mmol) of 4-dimethylamino benzoic acid was added and the mixture was stirred for 90 minutes. The solvent was evaporated under reduced pressure. The residue was treated with 300 mL methyl tert.-butyl ether, isolated by filtration and dried. 9.4 g (47 mmol) of 4-dimethylamino benzoic acid potassium salt was added to a solution of 10 g (56 mmol) of 2-bromoethyl acrylate in 40 mL dimethyl acetamide. 1 g of BHT was added and the mixture was heated to 60° C. for 2 hours. The reaction was allowed to cool down to room temperature. The formed potassium bromide was removed by filtration and 150 mL of methyl tert.-butyl ether was added. The mixture was extracted with 150 mL of water. The organic fraction was isolated, dried over MgSO$_4$ and evaporated under reduced pressure. The residue was redissolved in 150 mL of methyl tert.-butyl ether and extracted with 150 mL of a 1 M NaHCO$_3$-solution. The organic layer was dried over MgSO$_4$ and evaporated under reduced pressure. The residue was treated with water. COINI-2 precipitated from the medium, was isolated by filtration and dried. 4.3 g of COINI-2 was isolated.

STIN-1 is IRGACURE™ 2959, supplied by Ciba Specialty Chemicals:

STIN-2 is DAROCUR™ 1173, supplied by Ciba Specialty Chemicals:

STIN-3 is IRGACURE™ 184, supplied by Ciba Specialty Chemicals:

STIN-4 is IRGACURE™ 127, supplied by Ciba Specialty Chemicals:

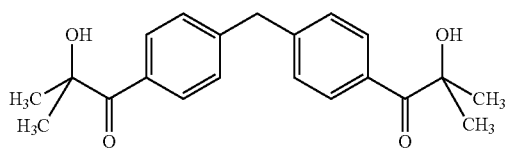 [SMILES: CC(C)(O)C(=O)c1ccc(Cc2ccc(C(=O)C(C)(C)O)cc2)cc1]

STIN-5 is a Norrish Type I photoinitiator (CASRN 110430-09-6):

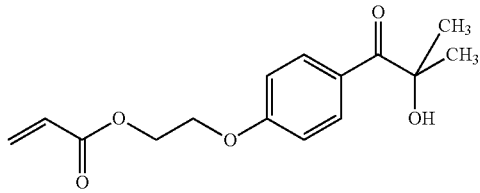 [SMILES: C=CC(=O)OCCOc1ccc(C(=O)C(C)(C)O)cc1]

and can be prepared as follows:

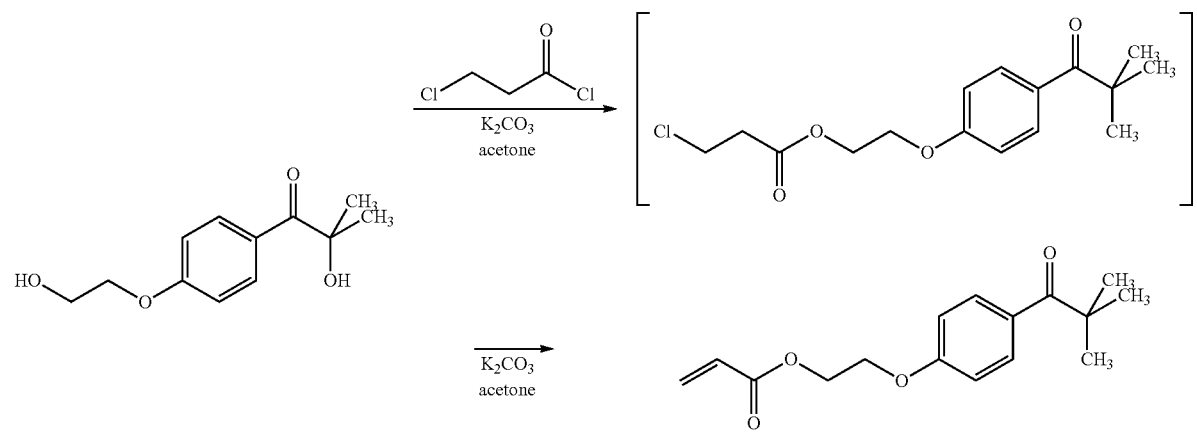

5.6 g (25 mmol) 2-hydroxy-1-[4-(2-hydroxyethoxy)phenyl]-2-methyl-1-propanone (STIN-1) and 60 mg BHT were dissolved in 100 mL acetone. 19 g (0.1375 mol) K$_2$CO$_3$ was added and the reaction mixture was cooled to −5° C. 9.5 mL (12.7 g, 0.1 mol) 3-chloropropionyl chloride was added over 30 minutes. The reaction mixture was refluxed for 10 hours and the conversion of 2-hydroxy-1-[4-(2-hydroxyethoxy) phenyl]-2-methyl-1-propanone to 4-(2-acryloyloxyethoxy) phenyl-2-hydroxy-2-propyl ketone was determined by GC as disclosed above. After 10 hours, the conversion proved to be 94.3%. Conventional isolation procedure can be used to isolate 4-(2-acryloyloxyethoxy)phenyl-2-hydroxy-2-propyl ketone.

STIN-6 is 1-{4-[2-(2,3-dihydroxy-propylsulfanyl)-ethoxy]-phenyl}-2-hydroxy-2-methyl-propan-1-one prepared as follows:

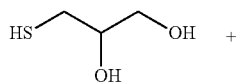

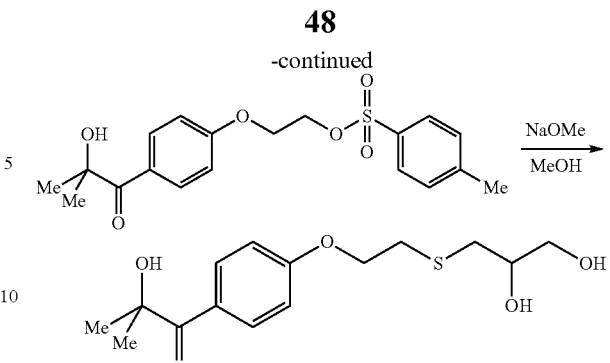

To a solution of 3-mercapto-1,2-propanediol (3.2 g, 0.03 mol) in methanol (70 mL), a solution of sodium methoxide in methanol (30 w %) (6.1 mL, 0.033 mol) in methanol (40 mL) was added drop wise and the reaction mixture was stirred for 30 minutes at room temperature. Toluene-4-sulfonic acid 2-[4-(2-hydroxy-2-methyl-propionyl)-phenoxy]-ethyl ester (11.4 g, 0.03 mol) was added and the reaction mixture was allowed to stir for 24 hours at room temperature. The solvent was evaporated under reduced pressure and the residual oil was treated with dichloromethane (100 mL) and filtered. Evaporation of the solvent provided a yellow oil, which was purified on a Prochrom LC80 Column using dichloromethane/ethyl acetate (50/50) as eluent and Kromasil Si60 10 μm as silica, to afford 4.7 g of a pale yellow solid.

STIN-7 is CASRN 15121-78-5, preparation: Harris et al., Synthetic Communications, 19(3-4), 529-35 (1989).

STIN-8 is CASRN 13020-57-0, supplied by Aldrich.

STIN-9 is CASRN 38933-94-7, preparation: Gustowski et al., J. Am. Chem. Soc., 108(24), 7553-60 (1986).

STIN-10 is N,N-Bis-(2-hydroxy-ethyl)-2-(9-oxo-9H-thioxanthen-2-yloxy)-acetamide prepared as follows:

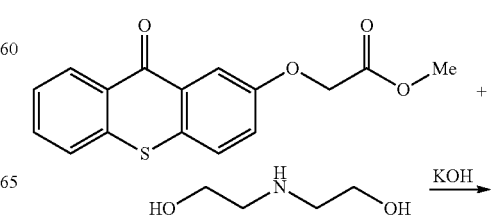

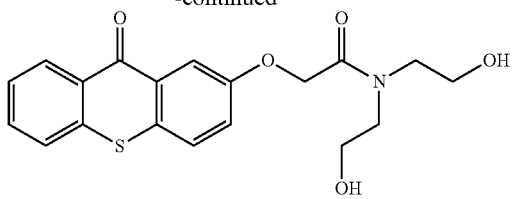

A solution of (9-oxo-9H-thioxanthen-2-yloxy)-acetic acid methyl ester (5.0 g, 16.6 mmol), diethanolamine (6.3 g, 60 mmol) and potassium hydroxide (0.05 g, 0.8 mol) was heated to 105° C. The reaction mixture was allowed to stir for 90 minutes. The reaction mixture was cooled to 30° C. and distilled water of 0° C. was added in portions. The crude N,N-bis-(2-hydroxy-ethyl)-2-(9-oxo-9H-thioxanthen-2-yloxy)-acetamide precipitated from the medium and was isolated by filtration. The crude N,N-bis-(2-hydroxy-ethyl)-2-(9-oxo-9H-thioxanthen-2-yloxy)-acetamide was treated with a mixture of distilled water (50 mL) and acetic acid (1 mL). N,N-bis-(2-hydroxy-ethyl)-2-(9-oxo-9H-thioxanthen-2-yloxy)-acetamide was isolated by filtration and washed with distilled water and methanol to yield 4.35 g of a yellow solid.

STIN-11 is [4-(3-dihydroxy-propoxy)phenyl]phenyl-methanone prepared as follows:

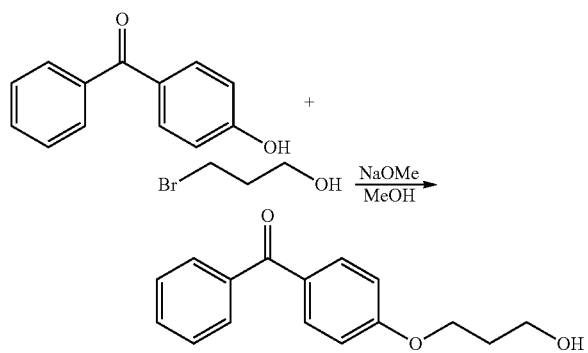

To a solution of 4-hydroxybenzophenone (7.5 g, 38 mmol) in methanol (20 mL), a solution of sodium methoxide in methanol (30 w %) (7 mL, 38 mmol) was added drop wise and the reaction mixture was stirred for 30 minutes at room temperature. 3-bromo-1-propanol (5.3 g, 38 mmol) was added in portions and the reaction mixture was allowed to stir at reflux temperature for 24 hours. The reaction mixture was cooled to room temperature and the solvent was removed under reduced pressure. The residue was treated with distilled water (300 mL) and the crude [4-(3-dihydroxy-propoxy)phenyl] phenyl-methanone was isolated by filtration. After drying, the crude [4-(3-dihydroxy-propoxy)phenyl]phenyl-methanone was treated in toluene (300 mL) at reflux. After cooling down to room temperature, the [4-(3-dihydroxy-propoxy)phenyl] phenyl-methanone was isolated by filtration to provide 5 g of a solid.

STIN-12 is 9-oxo-9H-thioxanthene-1-carboxylic acid-3-(4-acryloyloxy-butoxy)-2-hydroxy-propyl ester:

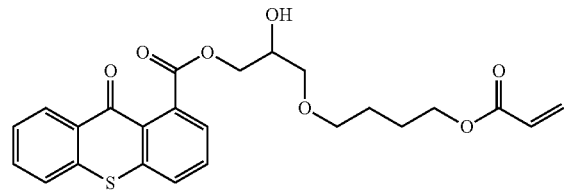 [SMILES: C=CC(=O)OCCCCOCC(O)COC(=O)c1cccc2sc3ccccc3c(=O)c12]

and was prepared as follows:

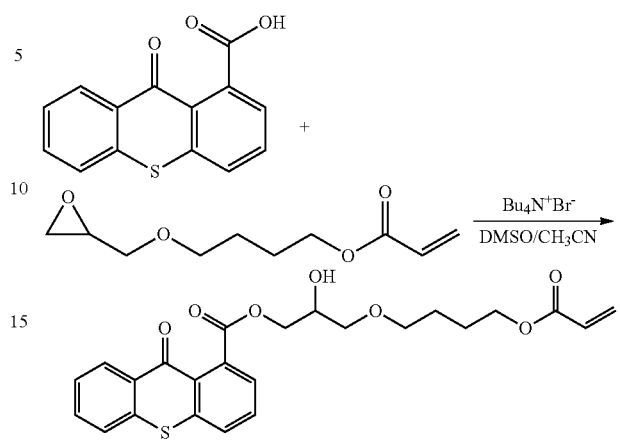

A reaction mixture containing 9-oxo-9H-thioxanthene-1-carboxylic acid (3.8 g, 15 mmol), acetonitrile (40 mL), dimethylsulfoxide (23 mL), tetrabutylammonium bromide (0.5 g, 1.5 mmol) and 2,6-di-tert-butyl-4-methylphenol (0.03 g, 0.122 mmol) was heated to reflux. At this temperature 4-hydroxybutylacrylate glycidylether (2.4 g, 12.2 mmol) was added and the mixture was allowed to stir at reflux temperature for 24 hours.

The mixture was cooled to room temperature and filtered to remove the residual, undissolved 9-oxo-9H-thioxanthene-1-carboxylic acid.

The filtrate was evaporated under reduced pressure.

The residual oil, which contains dimethylsulfoxide, was brought in distilled water. After stirring for 1 hour the aqueous layer was decanted off. The residue was dissolved in dichloromethane (100 mL) and extracted with a mixture of an aqueous solution of sodium hydroxide (1N) and distilled water (1/2).

The organic layer was separated, dried on $MgSO_4$, filtered and evaporated to provide 4.9 g of a yellow oil.

The product was purified on a SVP D40 Merck Np Column using dichloromethane/ethyl acetate (80/20) as eluent, to afford 2.6 g of a yellow oil.

STIN-13 is 9-oxo-9H-thioxanthene-2-carboxylic acid-3-(4-acryloyloxy-butoxy)-2-hydroxy-propyl ester:

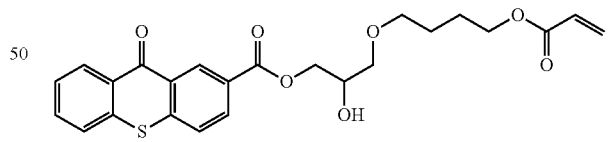

and was prepared as follows:

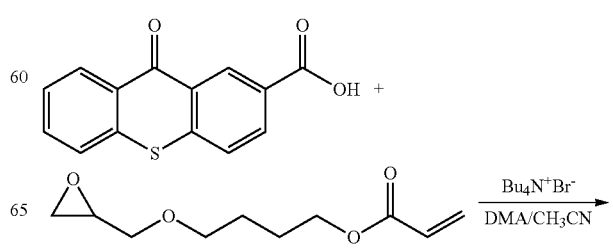

-continued

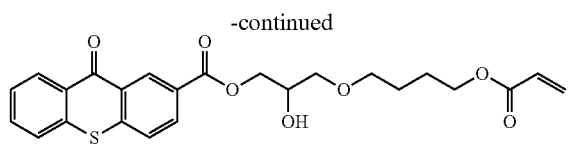

A reaction mixture containing 9-oxo-9H-thioxanthene-2-carboxylic acid (2.0 g, 7.8 mmol), acetonitrile (30 mL), dimethylacetamide (20 mL), tetrabutylammonium bromide (0.3 g, 0.78 mmol) and 2,6-di-tert-butyl-4-methylphenol (0.02 g, 0.0634 mmol) was heated to reflux. At this temperature 4-hydroxybutylacrylate glycidylether (1.3 g, 6.34 mmol) was added and the mixture was allowed to stir at reflux temperature for 24 hours.

The mixture was cooled to room temperature and filtered to remove the residual, undissolved 9-oxo-9H-thioxanthene-2-carboxylic acid.

The filtrate was evaporated under reduced pressure.

The residual oil was dissolved in methyl-tert-butylether (100 mL) and extracted with a mixture of an aqueous solution of sodium hydroxide (1N) and distilled water (1/4).

The organic layer was separated, dried on $MgSO_4$, filtered and evaporated to provide 2.5 g of a brown oil.

STIN-14 is 2-benzoyl-benzoic acid 3-(4-acryloyloxy-butoxy)-2-hydroxy-propyl ester:

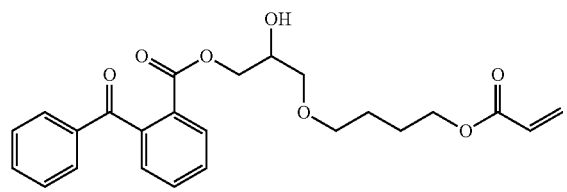 [SMILES: C=CC(=O)OCCCCOCC(O)COC(=O)c1ccccc1C(=O)c1ccccc1]

and was prepared as follows:

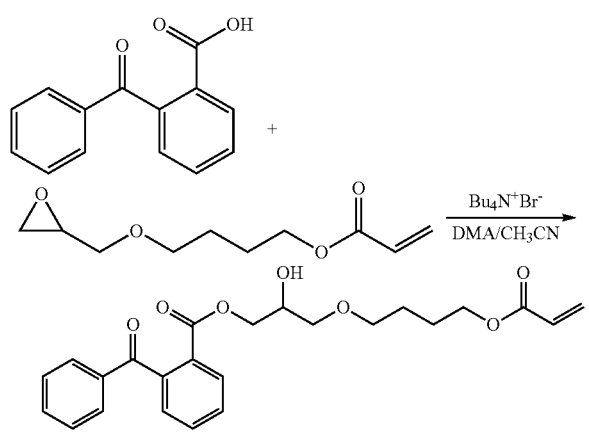

A reaction mixture containing 2-benzoyl benzoic acid (40.0 g), acetonitrile (300 mL), dimethylacetamide (10 mL), tetrabutylammonium bromide (5.6 g) and 2,6-di-tert-butyl-4-methylphenol (0.3 g) was heated to reflux.

At this temperature 4-hydroxybutylacrylate glycidylether (28.0 g) was added and the mixture was allowed to stir at reflux temperature for 16 hours.

The mixture was cooled to room temperature and the solvent was evaporated under reduced pressure.

The residual oil was dissolved in methyl-tert-butylether (300 mL) and extracted 3 times with a mixture of an aqueous solution of sodium hydroxide (1N) and distilled water (1/2.4).

The organic layer was separated, dried on $MgSO_4$, filtered and evaporated to provide 45.2 g of a brown oil.

STIN-15 is CASRN 1137-42-4, supplied by Aldrich:

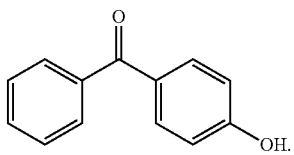 [SMILES: O=C(c1ccccc1)c1ccc(O)cc1]

STIN-16 is 2-(4-benzoyl-phenoxy)-N,N-bis-(2-hydroxyethyl)-acetamide prepared as follows:

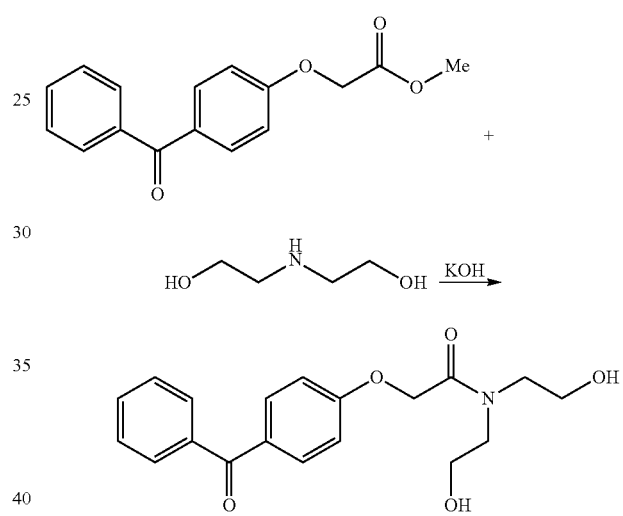

A solution of (4-benzoyl-phenoxy)-acetic acid methyl ester (10.8 g, 0.040 mol), diethanolamine (15.8 g, 0.15 mol) and potassium hydroxide (0.10 g, 0.0015 mol) was heated to 105° C. The reaction mixture was allowed to stir for 1 hour. The reaction mixture was cooled to room temperature and distilled water of 0° C. was added. The crude 2-(4-benzoyl-phenoxy)-N,N-bis-(2-hydroxy-ethyl)-acetamide precipitated as an oil. The aqueous phase was decanted off. The oil was dissolved in ethyl acetate (200 mL) and extracted 3 times with distilled water (50 mL). The organic layer was separated, dried over $MgSO_4$, filtered and evaporated under reduced pressure to provide 12.8 g of a white solid.

STIN-17 is 9-oxo-9H-thioxanthene-2-carboxylic acid 2-hydroxy-3-(2-methyl-acryloyl oxy)-propyl ester:

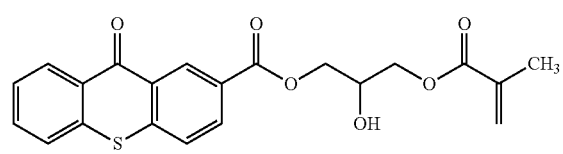 [SMILES: C=C(C)C(=O)OCC(O)COC(=O)c1ccc2sc3ccccc3c(=O)c2c1]

and prepared as follows:

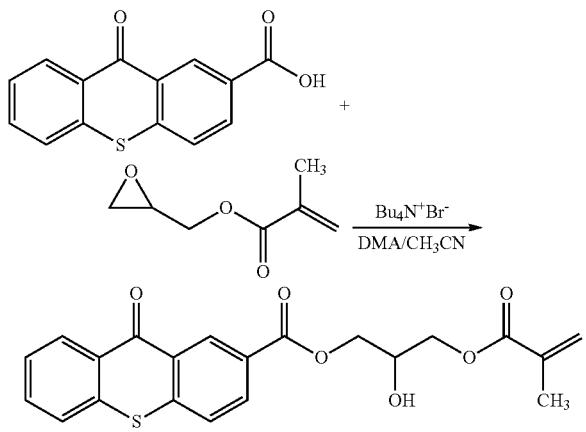

A reaction mixture containing 9-oxo-9H-thioxanthene-2-carboxylic acid (7.7 g, 30 mmol), acetonitrile (115 mL), dimethylacetamide (77 mL), tetrabutylammonium bromide (1.0 g, 3 mmol) and 2,6-di-tert-butyl-4-methylphenol (0.05 g, 0.244 mmol) was heated to reflux.

At this temperature glycidylmethacrylate (3.5 g, 24.4 mmol) was added and the mixture was allowed to stir at reflux temperature for 16 hours.

The mixture was cooled to room temperature and filtered to remove the residual, undissolved 9-oxo-9H-thioxanthene-2-carboxylic acid.

The filtrate was evaporated under reduced pressure.

The residual oil was dissolved in methyl-tert-butylether (100 mL) and extracted with a mixture of an aqueous solution of sodium hydroxide (1N) and distilled water (2.3/1).

The organic layer was separated, dried on $MgSO_4$, filtered and evaporated to provide 5.9 g of a brown oil. The product was purified on a Prochrom LC80 Column using Kromasil Si 60A 10 µm as silica and dichloromethane/ethyl acetate (80/20) as eluent, to afford 1.1 g of a yellow oil.

STIN-18 is [4-(2,3-dihydroxy-propoxy)-phenyl]phenyl-methanone:

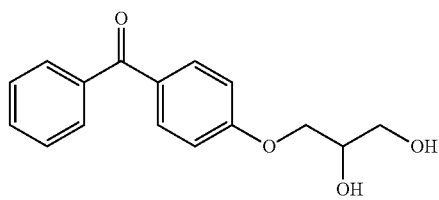

and prepared as follows:

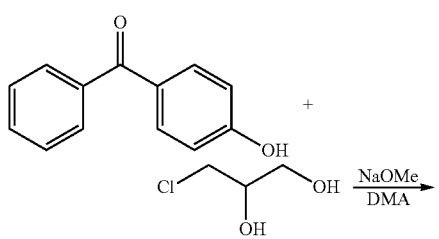

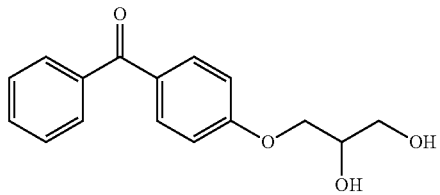 [SMILES: O=C(c1ccccc1)c1ccc(OCC(O)CO)cc1]

To a solution of 4-hydroxybenzophenone (79.3 g, 0.4 mol) in dimethylacetamide (300 mL), a solution of sodium methoxide in methanol (30 wt %) (74 mL, 0.04 mol) was added drop wise and the reaction mixture was stirred for 30 minutes at room temperature. 3-Chloro-1,2-propanediol (47.3 g, 0.43 mol) was added in portions and the reaction mixture was allowed to stir at reflux temperature for 24 hours. The reaction mixture was cooled to room temperature and the solvent was removed under reduced pressure. The residue was dissolved in dichloromethane (250 mL) and extracted twice with a mixture of an aqueous solution of sodium hydroxide (1N) and distilled water (1/6). The organic layer was separated, dried over $MgSO_4$, filtered and evaporated to provide 40.9 g of a yellow solid.

STIN-19 is 2-Benzoyl-benzoic acid 2-hydroxy-3-allyloxy-propyl ester:

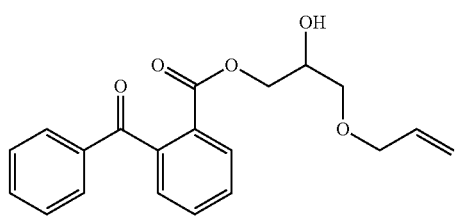 [SMILES: C=CCOCC(O)COC(=O)c1ccccc1C(=O)c1ccccc1]

and was prepared as follows:

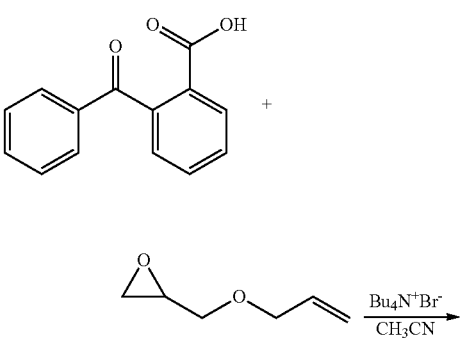

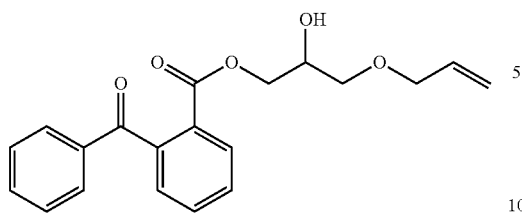

A reaction mixture containing 2-benzoyl-benzoic acid (14.7 g, 65 mmol), acetonitrile (100 mL), tetrabutylammonium bromide (2.1 g, 6.5 mmol) and 2,6-di-tert-butyl-4-methylphenol (0.1 g, 0.65 mol) was heated to 60° C. At this temperature allyl glycidyl ether (7.4 g, 65 mmol) was added and the mixture was allowed to stir at reflux temperature for 24 hours. The reaction mixture was cooled to room temperature and the solvent was removed under reduced pressure. The residual oil was dissolved in ethyl acetate (180 mL) and extracted twice with a mixture of an aqueous solution of sodium hydroxide (1N) and distilled water (1/6). The organic layer was separated, dried over MgSO$_4$, filtered and evaporated to provide 21.6 g of a brown oil.

STIN-20 is a difunctional α-hydroxyketone available from LAMBERTI under the tradename ESACURE™ One.

Measurement Methods

1. Measurement of the $^1$H-NMR Spectra

The $^1$H-NMR spectra were recorded as follows: a sample of 100 mg of each pre-formulation was dissolved in 0.7 mL CDCl$_3$. TMS was added as shift reference. The spectra were recorded on a 600 MHz Varian spectrometer (spectral window 10924 Hz (~18 ppm), acquisition time 5 s, relaxation delay 10 s, pulse width 45 deg, number of transients: 32).

2. Measurement of the $^1$F-NMR Spectra

The $^1$F-NMR spectra were recorded as follows: a sample of 100 mg of each pre-formulation was dissolved in 0.7 mL CDCl$_3$. 2 mg 4-fluoro-benzoic acid ethyl ester was added as standard. The spectra were recorded on a 400 MHz Varian spectrometer (spectral window 50000 Hz (~132 ppm), acquisition time 0.6 s, relaxation delay 10 s, pulse width: 45 deg, number of transients: 16).

3. Measurement of Viscosity

The viscosity of the formulations was measured using a Brookfield DV-II+ viscometer at 25° C. at 6 RPM.

4. Curing Degree

The curing degree was tested on a coating immediately after curing with UV light. The cured coating is rubbed with the means of a Q-tip. When the surface is not damaged, the coating is fully cured. When some of the cured coating can be damaged, the coating is only partly cured. When the whole cured coating is damaged, the coating is not cured.

5. Curing Speed

The curing speed was defined as the percentage of the maximum output of the lamp needed to cure the samples. The lower the number the higher curing speed. A sample was considered as fully cured at the moment scratching with a Q-tip caused no visual damage.

A percentage of more then 100% of the maximum output of the lamp means that the speed of the conveyer belt had to be reduced to get the sample fully cured at the maximum output of the lamp. The higher the percentage, the more the belt had to be slowed down. A curing speed of 160% means a belt speed of 12.5 m/min at the maximum output of the lamp. A percentage between 150% and 200% is considered as at the edge of practical use. A percentage above 200% is considered out of the range for practical use and no higher percentages are measured.

Example 1

This example illustrates the broad scope of photoinitiators containing a hydroxyl group that can be converted into polymerizable initiators in accordance with a preferred embodiment of the present invention by a particularly convenient synthetic procedure.

Pretreatment of the Ion Exchanger:

25 g of LEWATIT™ M600 MB was treated with 75 mL of 1 N sodium hydroxide solution and stirred for 2 hours. The ion exchanger was isolated by filtration, washed several times with water and dried until constant weight.

Synthesis:

The amount of the photoinitiator containing a hydroxyl group (=starting initiator) as specified in Table 3, was dissolved in the amount 2-(2-vinyloxyethoxy)ethyl acrylate (Ether-1), specified in Table 3. 1 mol % BHT, relative to 2-(2-vinyloxyethoxy)ethyl acrylate, was added, followed by the addition of 5 mol % of trifluoroacetic acid, relative to the hydroxyl containing photoinitiating moiety. The reaction was allowed to continue for the specified reaction time specified in Table 3 at 50° C. 25 g of the pretreated ion exchanger was added and the reaction mixture was stirred for 1 hour at room temperature. The ion exchanger was removed by filtration. The degree of conversion was determined using $^1$H-NMR. The presence of residual catalyst was determined, using $^{19}$F-NMR. The resulting polymerizable initiator was dissolved in Ether-1 and called the pre-formulation.

TABLE 3

| Starting Initiator | | Ether-1 | Reaction | Polymerizable | Pre- |
|---|---|---|---|---|---|
| Type | Amount | Amount | time (h) | initiator | formulation |
| STIN-1 | 4.1 g | 16 g | 4 | INI-4 | FVEEA-1 |
| STIN-2 | 3.5 g | 31.4 g | 16 | INI-8 | FVEEA-2 |
| STIN-3 | 7.5 g | 31.4 g | 3.5 | INI-27 | FVEEA-3 |
| STIN-4 | 7.5 g | 31.4 g | 4 | INI-28 | FVEEA-4 |
| STIN-5 | 7.5 g | 31.4 g | 6 | INI-29 | FVEEA-5 |
| STIN-6 | 3.0 g | 12.5 g | 3.5 | INI-30 | FVEEA-6 |
| STIN-7 | 7.5 g | 31.4 g | 3.5 | INI-31 | FVEEA-7 |
| STIN-8 | 2.7 g | 11.3 g | 2 | INI-32 | FVEEA-8 |
| STIN-9 | 2.3 g | 16.7 g | 4 (+48 h RT) | INI-33 | FVEEA-9 |
| STIN-10 | 1.9 g | 7.8 g | 2 | INI-34 | FVEEA-10 |
| STIN-11 | 3.7 g | 15.5 g | 2 | INI-35 | FVEEA-11 |
| STIN-12 | 5.8 g | 24.1 g | 2 | INI-36 | FVEEA-12 |
| STIN-13 | 2.5 g | 10.5 g | 2 | INI-37 | FVEEA-13 |
| STIN-14 | 7.5 g | 31.4 g | 2 | INI-38 | FVEEA-14 |
| STIN-15 | 4.5 g | 31.4 g | 6.5 | INI-1 | FVEEA-15 |
| STIN-16 | 5.0 g | 20.9 g | 2 | INI-9 | FVEEA-16 |
| STIN-17 | 7.5 g | 31.4 g | 2 (+15 h RT) | INI-39 | FVEEA-17 |
| STIN-18 | 7.5 g | 31.4 g | 2 | INI-7 | FVEEA-18 |
| STIN-19 | 6.5 g | 27.2 g | 2 | INI-40 | FVEEA-19 |

From the $^1$H-NMR-analysis, it became apparent that the photoinitiators containing a hydroxyl group were completely converted into asymmetrical acetals. From the $^{19}$F-NMR analysis, it became apparent that the catalyst was as good as completely removed from the pre-formulations upon treatment with an ion exchanger. Sometimes, trace amount (0.01% w/w or lower) were detectable.

The $^1$H-NMR-assignment of some initiators according to a preferred embodiment of the present invention is exemplified below.

INI-1:
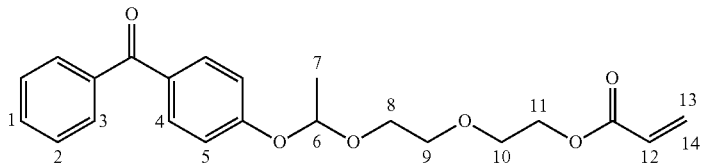 [SMILES: C=CC(=O)OCCOCCOC(C)Oc1ccc(C(=O)c2ccccc2)cc1]
| | | |
|---|---|---|
| | 1 | 7.59 |
| | 2 | 7.48 |
| | 3 | 7.76 |
| | 4 | 7.79 |
| | 5 | 7.19 |
| | 6 | 5.59 |
| | 7 | 1.58 |
| | 8 | 3.60-3.80 |
| | 9 | 3.60-3.80 |
| | 10 | 3.60-3.80 |
| | 11 | 4.29 |
| | 12 | 6.12 |
| | 13 | 6.40 |
| | 14 | 5.82 |
INI-8:
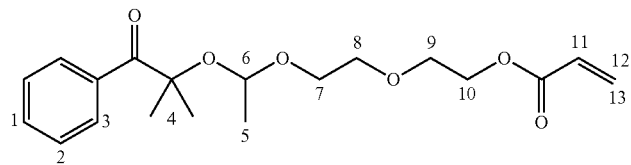 [SMILES: C=CC(=O)OCCOCCOC(C)OC(C)(C)C(=O)c1ccccc1]
| | | |
|---|---|---|
| | 1 | 7.48 |
| | 2 | 7.40 |
| | 3 | 8.23 |
| | 4 | 1.54 |
| | 5 | 1.27 |
| | 6 | 4.82 |
| | 7 | 3.40-3.70 |
| | 8 | 3.40-3.70 |
| | 9 | 3.40-3.70 |
| | 10 | 4.28 |
| | 11 | 6.12 |
| | 12 | 5.82 |
| | 13 | 6.40 |
INI-28:
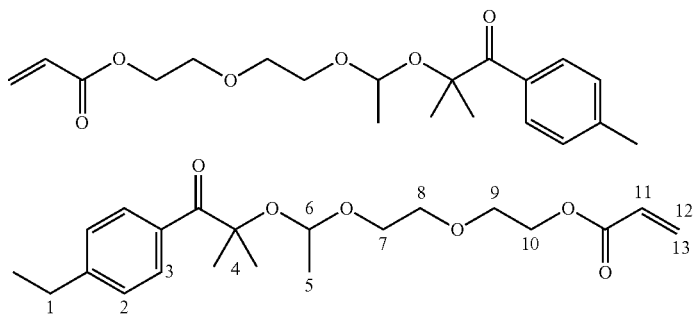
| | | |
|---|---|---|
| | 1 | 4.12 |
| | 2 | 7.22 |
| | 3 | 8.18 |
| | 4 | 1.53 |
| | 5 | 1.24 |
| | 6 | 4.82 |
| | 7 | 3.40-3.70 |
| | 8 | 3.40-3.70 |
| | 9 | 3.40-3.70 |
| | 10 | 4.30 |
| | 11 | 6.12 |
| | 12 | 5.82 |
| | 13 | 6.40 |
INI-32:
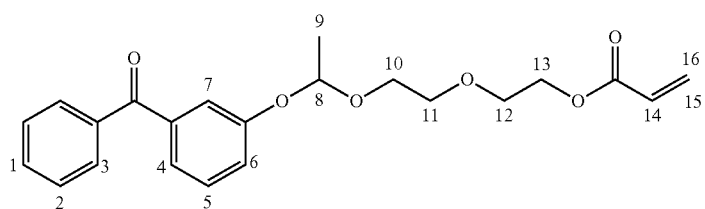 [SMILES: C=CC(=O)OCCOCCOC(C)Oc1cccc(C(=O)c2ccccc2)c1]
| | | |
|---|---|---|
| | 1 | 7.58 |
| | 2 | 7.48 |
| | 3 | 7.59 |
| | 4 | 7.39 |
| | 5 | 7.38 |
| | 6 | 7.26 |
| | 7 | 7.46 |
| | 8 | 5.51 |
| | 9 | 1.52 |
| | 10 | 3.60-3.80 |
| | 11 | 3.60-3.80 |
| | 12 | 3.60-3.80 |
| | 13 | 4.28 |
| | 14 | 6.12 |
| | 15 | 5.82 |
| | 16 | 6.40 |
INI-35:
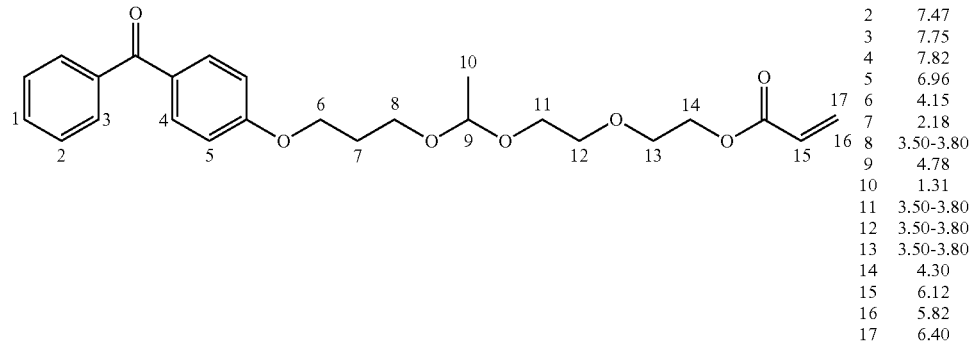
| | | |
|---|---|---|
| | 1 | 7.56 |
| | 2 | 7.47 |
| | 3 | 7.75 |
| | 4 | 7.82 |
| | 5 | 6.96 |
| | 6 | 4.15 |
| | 7 | 2.18 |
| | 8 | 3.50-3.80 |
| | 9 | 4.78 |
| | 10 | 1.31 |
| | 11 | 3.50-3.80 |
| | 12 | 3.50-3.80 |
| | 13 | 3.50-3.80 |
| | 14 | 4.30 |
| | 15 | 6.12 |
| | 16 | 5.82 |
| | 17 | 6.40 |

And some of the reactants:

Ether-1:

|   |      |
|---|------|
| 1 | 6.42 |
| 2 | 5.85 |
| 3 | 6.17 |
| 4 | 4.32 |
| 5 | 3.77 |
| 6 | 3.77 |
| 7 | 3.85 |
| 8 | 6.5  |
| 9 | 4.03 |
| 10| 4.19 |

STIN-1:

|   |      |
|---|------|
| 1 | 2.28 |
| 2 | 4.01 |
| 3 | 4.18 |
| 4 | 6.98 |
| 5 | 8.08 |
| 6 | 1.61 |
| 7 | 4.28 | and

STIN-15:

|   |      |
|---|------|
| 1 | 7.33 |
| 2 | 6.92 |
| 3 | 7.76 |
| 4 | 7.74 |
| 5 | 7.45 |
| 6 | 7.55 |

Example 2

This example illustrates the polymerizable initiators in accordance with a preferred embodiment of the present invention can be prepared with different vinylether monomers according to Formula (II).

Synthesis:

The amount of the hydroxyl containing photoinitiating photoinitiator (=starting initiator) as specified in Table 4, was dissolved in the amount of a vinyl ether containing monomer as specified in Table 4. 1 mol % BHT, relative to vinyl ether containing monomer, was added, followed by the addition of 5 mol % of trifluoroacetic acid, relative to the hydroxyl containing photoinitiating moiety. The reaction was allowed to continue for the specified reaction time at 50° C. 25 g of the pretreated ion exchanger was added and the reaction mixture was stirred for 1 hour at room temperature. The ion exchanger was removed by filtration. The degree of conversion was determined using $^1$H-NMR. The presence of residual catalyst was determined, using $^{19}$F-NMR. The resulting polymerizable initiator was dissolved in the monomer used as reactant and called the pre-formulation.

TABLE 4

| Starting Initiator | | Monomer | | Reaction time (h) | Polymerizable initiator | Pre-formulation |
|---|---|---|---|---|---|---|
| Type | Amount | Type | Amount | | | |
| STIN-15 | 7.5 g | Ether-2 | 31.4 g | 2 | INI-44 | FVEEM-1 |
| STIN-15 | 7.5 g | Ether-4 | 30.0 g | 2 | INI-15 | FVEM-1 |
| STIN-15 | 7.5 g | Ether-5 | 30.6 g | 2 | INI-14 | FVEA-1 |
| STIN-2 | 7.5 g | Ether-2 | 30.9 g | 15 | INI-11 | FVEEM-2 |

TABLE 4-continued

| Starting Initiator | | Monomer | | Reaction time (h) | Polymerizable initiator | Pre-formulation |
|---|---|---|---|---|---|---|
| Type | Amount | Type | Amount | | | |
| STIN-3 | 7.5 g | Ether-2 | 30.9 g | 21 | INI-43 | FVEEM-3 |
| STIN-18 | 7.5 g | Ether-2 | 30.9 g | 2 | INI-42 | FVEEM-4 |
| STIN-20 | 7.5 g | Ether-2 | 30.9 g | 3.5 | INI-41 | FVEEM-5 |

From the $^1$H-NMR-analysis, it became apparent that the hydroxyl functional groups from the hydroxyl containing photoinitiating moieties were completely converted into asymmetrical acetals. From the $^{19}$F-NMR analysis, it became apparent that the catalyst was as good as completely removed from the pre-formulations upon treatment with an ion exchanger. Sometimes, trace amount (0.01% w/w or lower) were detectable.

Example 3

This example illustrates the need for a catalyst to convert the photoinitiators containing a hydroxyl group into polymerizable photoinitiators according to a preferred embodiment of the present invention.

Synthesis:

A set of four starting initiators were allowed to react as specified in Table 5. The degree of conversion was determined using TLC chromatography.

TABLE 5

| Starting Initiator | | Ether-1 | Reaction | Reaction | Degree of |
|---|---|---|---|---|---|
| Type | Amount | Amount | temperature | time | conversion |
| STIN-2 | 7.5 g | 31.4 g | 50° C. | 72 h | No conversion (1) |
| STIN-1 | 7.5 g | 31.4 g | 50° C. | 72 h | No conversion (2) |
| STIN-15 | 7.5 g | 31.4 g | 50° C. | 72 h | No conversion (3) |
| STIN-20 | 7.5 g | 31.4 g | 50° C. | 72 h | No conversion (4) |

(1) reference: INI-8: $R_f$=0.42, Partisil KC18F, supplied by Whatman, eluent MeOH/NaCl 0.5 M 80/20.

(2) reference: INI-4: $R_f$=0.32, Partisil KC18F, supplied by Whatman, eluent MeOH/NaCl 0.5 M 80/20.

(3) reference: INI-1: $R_f$=0.38, Partisil KC18F, supplied by Whatman, eluent MeOH/NaCl 0.5 M 80/20

(4) reference: INI-6: $R_f$=0.33, Partisil KC18F, supplied by Whatman, eluent MeOH/NaCl 0.5 M 90/10

From Table 5, it becomes apparent that a catalyst is needed, to convert hydroxyl containing photoinitiators to polymerizable photoinitiators according to a preferred embodiment of the present invention.

Example 4

This example illustrates the possibility of using a crosslinked resin as catalyst to convert hydroxyl containing photoinitiators into polymerizable initiators according to a preferred embodiment of the present invention.

Synthesis:
a) Derivatization of 4-hydroxy-benzophenone (STIN-15)

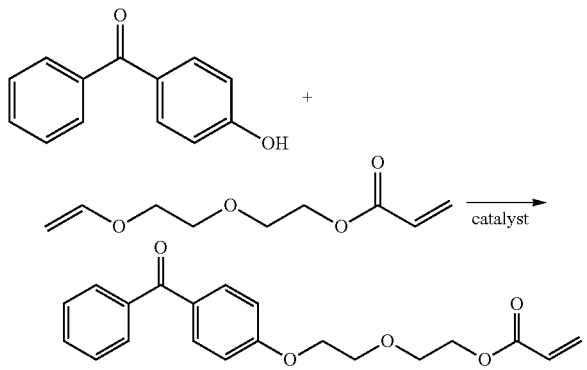

Cross-Linked Poly(Vinylpyridine) Tosylate as Catalyst:

7.5 g (38 mmol) 4-hydroxy-benzophenone was dissolved in 30 mL 2-(2-vinyloxyethoxy)ethyl acrylate. 40 mg BHT was added. 0.9 g cross-linked poly(vinylpyridine) tosylate, cross-linked with 2% divinyl benzene (supplied by Aldrich), was added. The reaction mixture was heated to 55° C. and the reaction was allowed to continue for 16 hours. A TLC analysis indicated a full conversion of the phenolic group (Partisil KC18F, supplied by Whatman, eluent: MeOH/NaCl 0.5 M; $R_f$=0.39). The catalyst was removed by filtration and the solution of INI-1 in 2-(2-vinyloxyethoxy)ethyl acrylate can directly be used to formulate radiation curable compositions.

Cross-Linked Poly(Vinylpyridine) Chlorohydrate as Catalyst:

7.5 g (38 mmol) 4-hydroxy-benzophenone was dissolved in 30 mL 2-(2-vinyloxyethoxy)ethyl acrylate. 40 mg BHT was added. 0.9 g cross-linked poly(vinylpyridine) chlorohydrate, cross-linked with 2% divinyl benzene (supplied by Aldrich), was added. The reaction mixture was heated to 55° C. and the reaction was allowed to continue for 16 hours. A TLC analysis indicated a full conversion of the phenolic group (Partisil KC18F, supplied by Whatman, eluent MeOH/NaCl 0.5 M 80/20). The catalyst was removed by filtration and the solution of INI-1 in 2-(2-vinyloxyethoxy)ethyl acrylate can directly be used to formulate radiation curable compositions.

B) Derivatization of STIN-1:

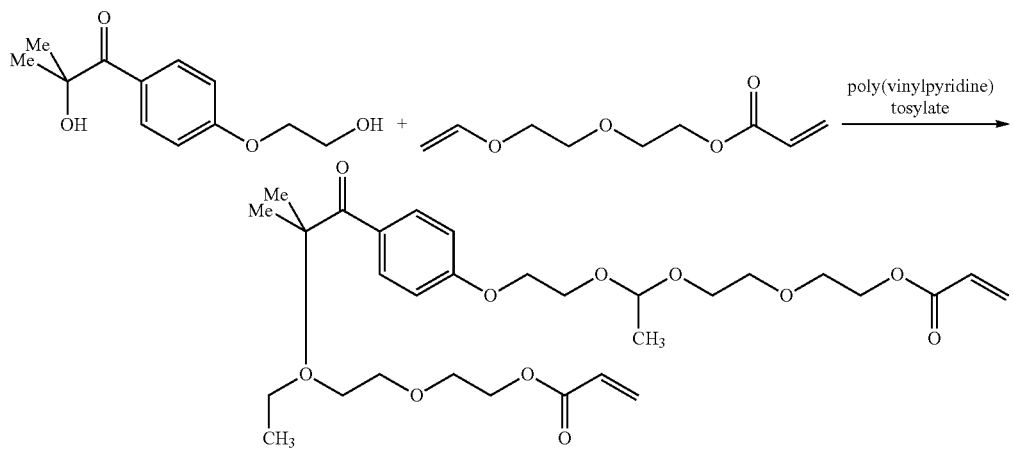

Cross-Linked Poly(Vinylpyridine) Tosylate as Catalyst:

7.5 g (33 mmol) STIN-1 was dissolved in 30 mL 2-(2-vinyloxyethoxy)ethyl acrylate. 70 mg BHT was added. The reaction mixture was heated to 55° C. 0.94 g cross-linked poly(vinylpyridine) tosylate, cross-linked with 2% divinyl benzene (supplied by Aldrich), was added and the reaction was allowed to continue for 16 hours. A TLC analysis indicated a full conversion of both the primary and tertiary alcohol (Partisil KC18F, supplied by Whatman, eluent: MeOH/NaCl 0.5 M; $R_f$=0.37). The catalyst was removed by filtration and the solution of INI-4 in 2-(2-vinyloxyethoxy)ethyl acrylate can directly be used to formulate radiation curable compositions.

c) Derivatization of STIN-4:

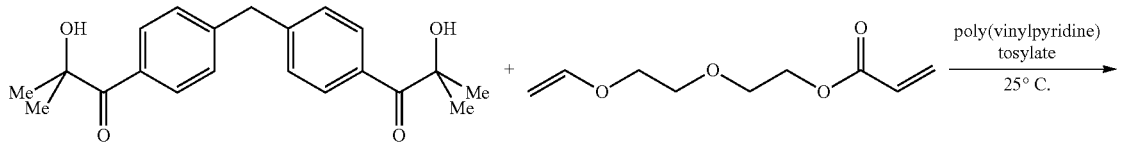

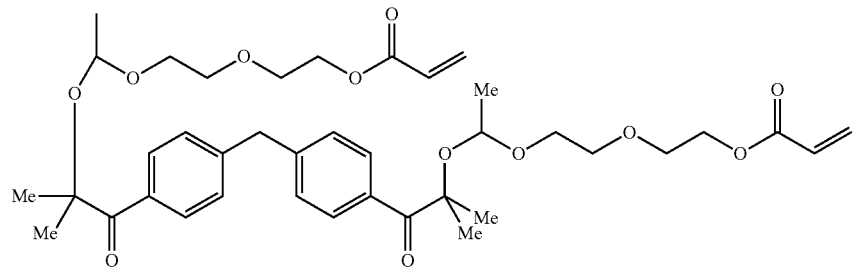

225 g (0.66 mol) STIN-4 was dissolved in 900 mL 2-(2-vinyloxyethoxy)ethyl acrylate at 55° C. 1.5 g BHT was added. The reaction mixture was cooled down to room temperature. STIN-4 partially precipitated from the medium. 9.5 g cross-linked poly(vinylpyridine) tosylate, cross-linked with 2% divinyl benzene (supplied by Aldrich) was added and the reaction was allowed to continue for 24 hours at room temperature. TLC analysis indicated full conversion of the hydroxyl groups (Partisil KC18F, supplied by Whatman, eluent: MeOH/NaCl 0.5 M; $R_f$=0.46). The catalyst was removed by filtration and the solution of INI-28 in 2-(2-vinyloxyethoxy)ethyl acrylate can directly be used to formulate radiation curable compositions.

Example 5

The applicability of the present invention for the design of polymeric photoinitiators is illustrated with the preparation of initiator PG.

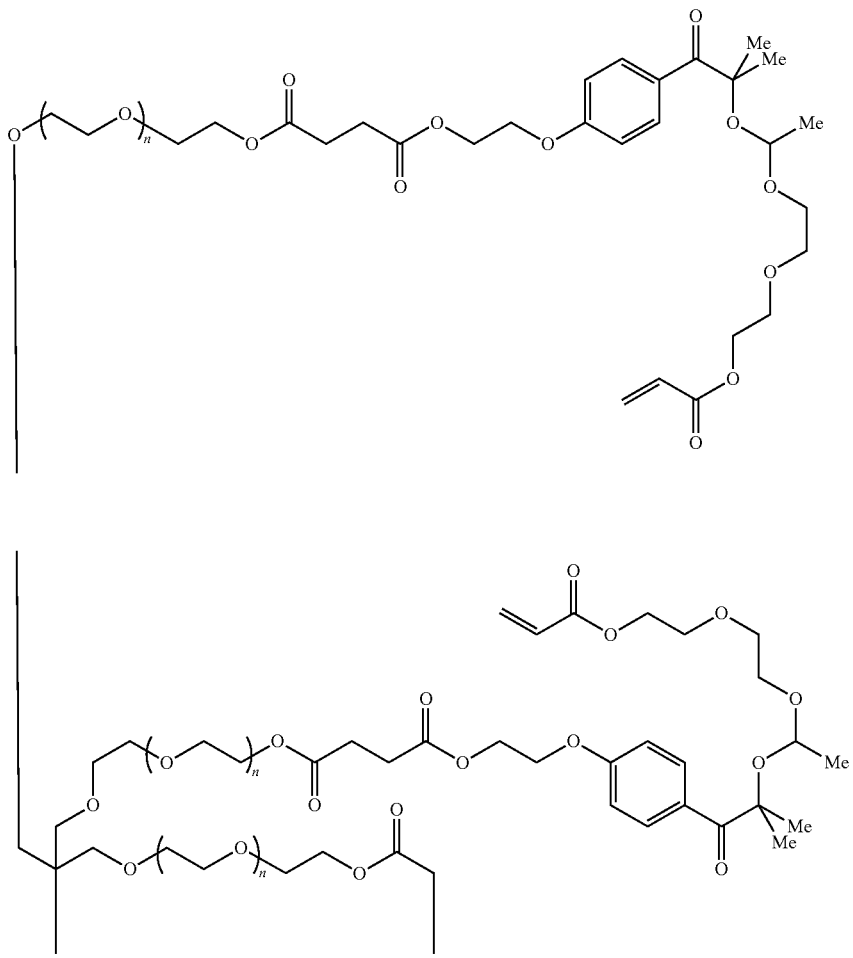

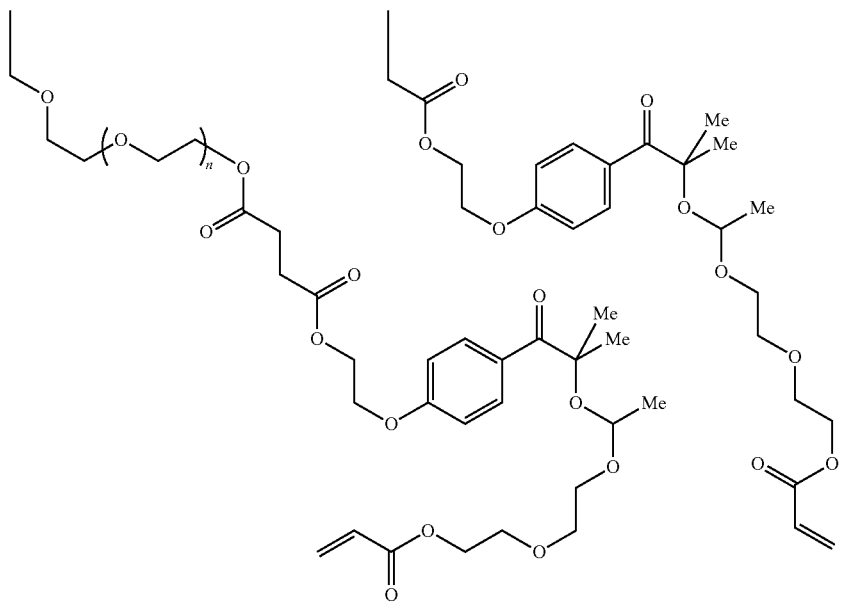

Synthesis:
Step 1: Succinic acid mono-{2-[4-(2-hydroxy-2-methyl-propionyl)-phenoxy]-ethyl}ester

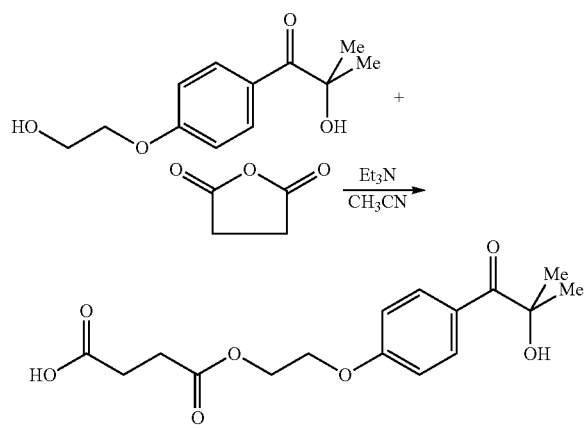

To a suspension of STIN-1 (44.9 g, 0.2 mol) in acetonitrile (500 mL), triethylamine (44.5 g, 0.44 mol) was added, to result in a clear solution. Succinic anhydride (22.0 g, 0.22 mol) was added and the reaction mixture was allowed to stir at room temperature for 24 hours. After evaporation of the solvent, the residual oil was dissolved in a mixture of distilled water (500 mL) and an aqueous solution of sodium hydroxide (1N) (110 mL) and extracted with ethyl acetate (500 mL). The organic layer was separated and the aqueous layer was acidified to pH=1 with an aqueous solution of hydrochloric acid and extracted twice with dichloromethane (500 mL). The organic layer was separated, dried over MgSO$_4$, filtered and evaporated. The residue was treated with n-hexane and cooled to 3° C. for 15 hours. The crude succinic acid mono-{2-[4-(2-hydroxy-2-methyl-propionyl)-phenoxy]-ethyl}ester was isolated by filtration. The product was purified on a Prochrom LC80 Column using dichloromethane/ethyl acetate (75/25) as eluent and Kromasil Si60 10 mm as silica, to afford 20.6 g of a pale yellow solid.

Step 2: The esterification of pentaerythritol ethoxylate

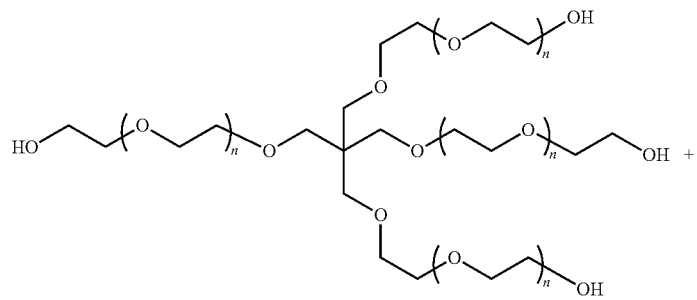

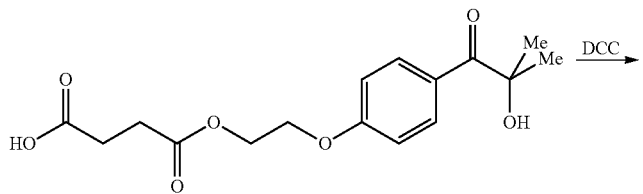

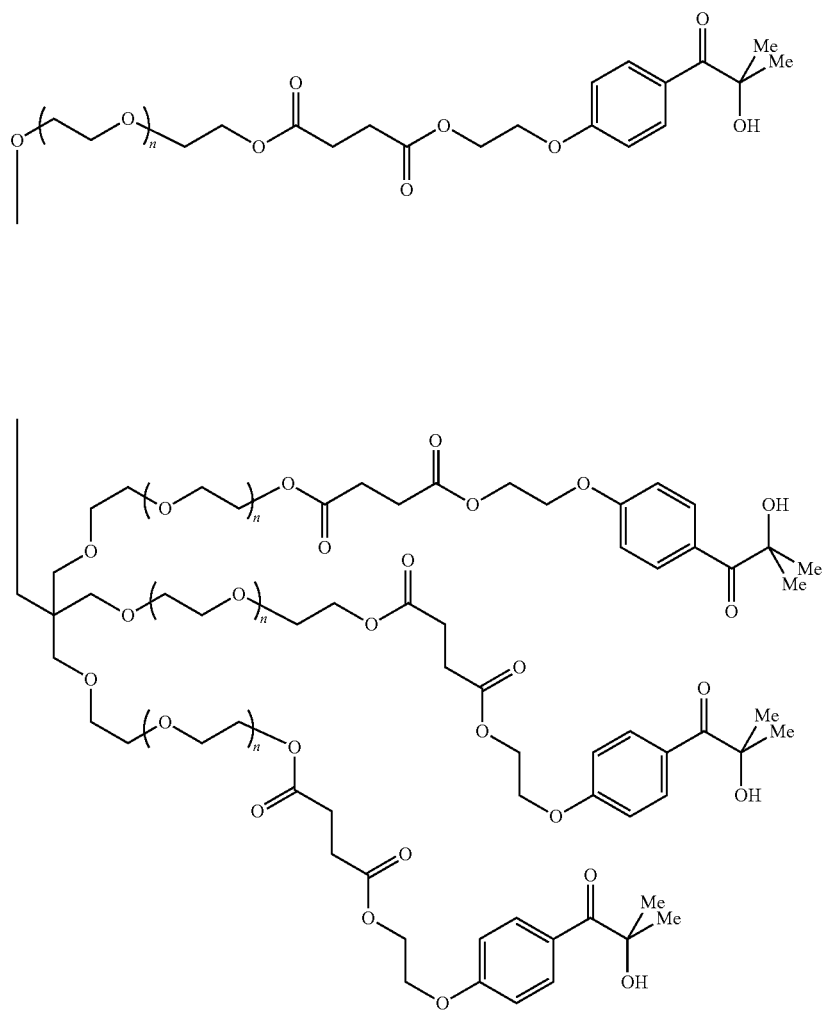

To a solution of succinic acid mono-{2-[4-(2-hydroxy-2-methyl-propionyl)-phenoxy]-ethyl}ester (48.6 g, 0.15 mol) in toluene (350 mL), pentaerythritol ethoxylate 15/4 (29.9 g, 0.0375 mol), N,N'-dicyclohexylcarbodiimide (34.0 g, 0.165 mol) and dimethylaminopyridine (4.6 g, 0.0375 mol) were added and the reaction mixture was heated to reflux and allowed to stir at this temperature for 24 hours. The reaction mixture was cooled to room temperature and the precipitated residues were removed by filtration. The precipitated residues were washed with acetone. After evaporation of the solvent, the residue was dissolved in ethyl acetate (300 mL) and extracted with a mixture of distilled water (250 mL) and an aqueous solution of hydrochloric acid (6N) (50 mL). The organic layer was isolated, dried over $MgSO_4$, filtered and evaporated to provide 83 g of a yellow oil.

Step 3: Conversion of the hydroxyl groups:
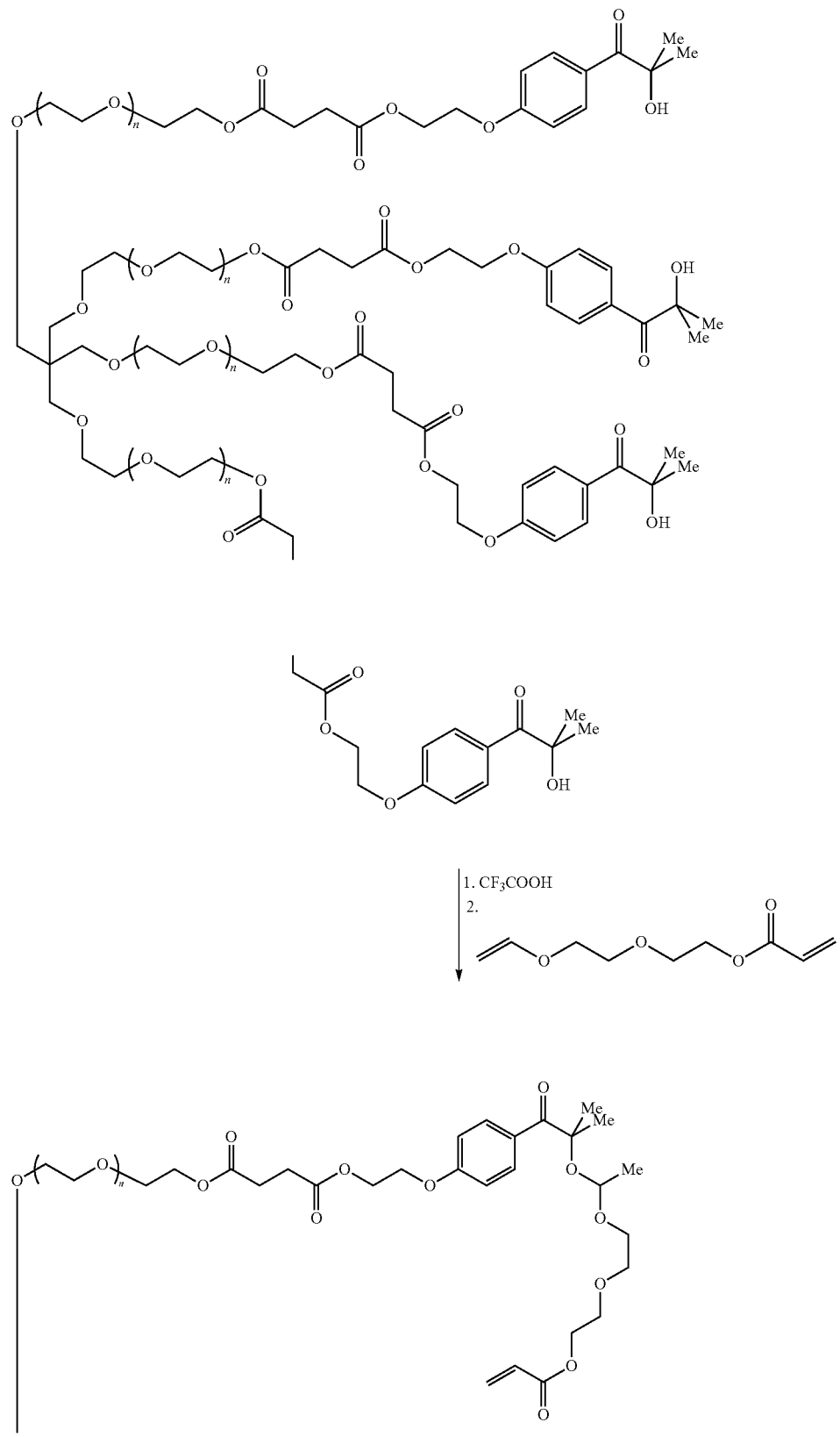

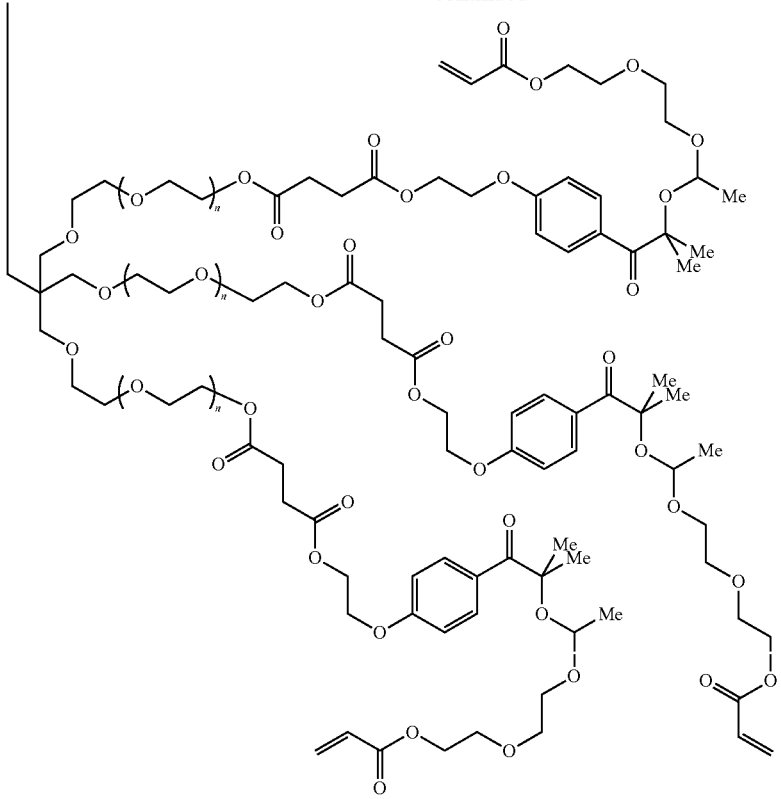

A mixture containing the polymeric a-hydroxyketone Norrish type I photoinitiator (7.5 g, 0.017 mol), 2-(2-vinyloxy-ethoxy)ethylacrylate (30 mL), 2,6-di-tert-butyl-4-methylphenol (0.0.4 g, 0.00017 mol) was stirred for 30 minutes at 55° C. to result in a clear solution. After cooling down to room temperature, trifluoroacetic acid (0.1 g, 0.85 mol) was added and the reaction mixture was heated to 55° C. and allowed to stir for 3.5 hours. The reaction mixture was treated with pretreated LEWATIT™ M600 MB for 1 hour. The ion exchanger was removed by filtration to provide a 35.5 w % solution of PG in Ether-1 (FVEEA-20).

Example 6

This example illustrates the possibility of preparing the initiators according to a preferred embodiment of the present invention in a monomer of preference, to be used in the final formulation.

Synthesis:

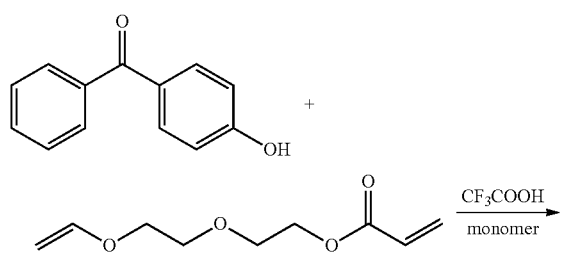

-continued

![structure]

5 mol % of trifluoroacetic acid relative to 4-hydroxy-benzophenone (STIN-15) was added to the mixture as specified in Table 6. The reaction was allowed to continue to completion. The degree of conversion was determined using thin layer chromatography (Partisil KC18F, supplied by Whatman, eluent: MeOH/NaCl 0.5 M; $R_f$=0.39). The reaction time and temperature to get complete conversion in the different monomers is given in Table 6. The catalyst was removed by adding 25 g of the pretreated ion exchanger and the reaction mixture was stirred for 1 hour at room temperature. The ion exchanger was removed by filtration.

TABLE 6

| Amount of STIN-15 | Mixture of monomers | | | Reaction time for complete conversion |
|---|---|---|---|---|
| | ETHER-1 Amount | Monomer of preference Type | Amount | |
| 2.5 g | 4.5 g | SR339C | 6.0 g | 16 hour at room temperature |
| 2.5 g | 5.5 g | SR9003 | 5.8 g | 16 hour at room temperature |
| 2.5 g | 4.5 g | SR8335 | 5.7 g | 16 hour at room temperature |
| 7.5 g | 7.4 g | SR508 | 22.9 mL | 16 hour at 50° C. |

From Table 6, it becomes apparent that the initiators according to a preferred embodiment of the present invention can be prepared in a broad scope of monomer mixtures, if required for a specific application. However, for a skilled person it will be clear that if a monomer is selected which also contains a hydroxyl group and which is added in a large amount that this could result in a lower conversion to a polymerizable photoinitiator. In such a case the monomer containing a hydroxyl group is preferably added after complete conversion of the photoinitiator containing a hydroxyl group to a polymerizable photoinitiator.

Example 7

This example illustrates the photoreactivity of polymerizable Norrish type I photoinitiators according to a preferred embodiment of the present invention when used as single initiator.

Preparation of Radiation Curable Compositions

The comparative radiation curable compositions COMP-1 to COMP-3 and the inventive radiation curable compositions INV-1 to INV-4 were prepared according to Table 7. The weight % (wt %) was based on the total weight of the radiation curable compositions. Dibutyl phthalate was added to the radiation curable compositions as an internal reference to allow analysis of extractable residues. The pre-formulations, prepared in the preceding examples were directly used in the radiation curable compositions. The comparative initiators were used as pure compounds.

TABLE 7

| wt % of | INV-1 | INV-2 | INV-3 | INV-4 | COMP-1 | COMP-2 | COMP-3 |
|---|---|---|---|---|---|---|---|
| Ether-1 | 29.0 | 43.5 | 27.0 | 14.0 | 73.0 | 71.5 | 66.5 |
| M600 | 20.0 | 20.0 | 20.0 | 20.0 | 20.0 | 20.0 | 20.0 |
| FVEEA-4 | 50.0 | — | — | — | — | — | — |
| FVEEA-7 | — | 35.5 | — | — | — | — | — |
| FVEEA-2 | — | — | 52.0 | — | — | — | — |
| FVEEA-20 | — | — | — | 65.0 | — | — | — |
| STIN-2 | — | — | — | — | 6.0 | — | — |
| STIN-3 | — | — | — | — | — | 7.5 | — |
| STIN-4 | — | — | — | — | — | — | 12.5 |
| Dibutyl phthalate | 1.0 | 1.0 | 1.0 | 1.0 | 1.0 | 1.0 | 1.0 |

Evaluation and Results

The curing degree of the inventive radiation curable compositions INV-1 to INV-4 and the comparative radiation curable compositions COMP-1 to COMP-3 was evaluated. The inventive radiation curable compositions INV-1 to INV-4 and the comparative radiation curable compositions COMP-1 to COMP-3 were coated on a PET100 substrate using a bar coater and a 10 μm wired bar. The coatings were cured using a Fusion DRSE-120 conveyer, equipped with a Fusion VPS/1600 lamp (D-bulb), which transported the samples under the UV-lamp on a conveyer belt at a speed of 20 m/min. The lamp was used at full power. The samples were cured, using nitrogen inertisation. Before a coated sample was placed on the conveyer belt, the coated sample was mounted on a metal plate and on top of the plate a metal frame of 1 cm height with a non UV-absorbing quartz glass window was placed, so that a sealed chamber was formed with the coated sample inside. Then, the trapped air in the chamber was replaced by nitrogen gas by introducing pure nitrogen gas into the chamber for 30 seconds. The curing degree was determined.

The results are summarized in Table 8.

TABLE 8

| Radiation curable composition | Curing degree |
|---|---|
| INV-1 | Fully cured |
| INV-2 | Fully cured |
| INV-3 | Fully cured |
| INV-4 | Fully cured |
| COMP-1 | Fully cured |
| COMP-2 | Fully cured |
| COMP-3 | Fully cured |

From Table 8, it becomes apparent that the photoinitiators according to a preferred embodiment of the present invention result in fully cured coatings, comparable to state-of-the-art Norrish type I initiators.

Example 8

This example illustrates the photoreactivity of Norrish type I initiators, according to a preferred embodiment of the present invention, when used in combination with state-of-the-art polymerizable initiators and coinitiators.

Preparation of Radiation Curable Compositions

The comparative radiation curable composition COMP-4 and inventive radiation curable compositions INV-5 to INV-11 were prepared according to Table 9. The weight % (wt %) was based on the total weight of the radiation curable compositions. Dibutyl phthalate was added to the radiation curable compositions as an internal reference to allow analysis of extractable residues. The pre-formulations, prepared in the preceding examples were directly used in the radiation curable compositions.

TABLE 9

| wt % of | INV-5 | INV-6 | INV-7 | INV-8 | INV-9 | INV-10 | INV-11 | COMP-4 |
|---|---|---|---|---|---|---|---|---|
| Ether-1 | 2.5 | 9.0 | 7.0 | 16.5 | 13.0 | 1.0 | 0.5 | 9.0 |
| M600 | 20.0 | 20.0 | 20.0 | 20.0 | 20.0 | 20.0 | 20.0 | 20.0 |
| FVEEA-4 | 36.5 | — | — | — | — | — | — | — |
| FVEEA-5 | — | 30.0 | — | — | — | — | — | — |
| FVEEA-6 | — | — | 32 | — | — | — | — | — |
| FVEEA-3 | — | — | — | 22.5 | — | — | — | — |
| FVEEA-7 | — | — | — | — | 26.0 | — | — | — |
| FVEEA-2 | — | — | — | — | — | 38.0 | — | — |
| FVEEA-1 | — | — | — | — | — | — | 38.5 | — |
| STIN-5 (*) | — | — | — | — | — | — | — | 30.0 |
| Type II (*) | 20.0 | 20.0 | 20.0 | 20.0 | 20.0 | 20.0 | 20.0 | 20.0 |
| COINI-1 (*) | 20.0 | 20.0 | 20.0 | 20.0 | 20.0 | 20.0 | 20.0 | 20.0 |
| Dibutyl phthalate | 1.0 | 1.0 | 1.0 | 1.0 | 1.0 | 1.0 | 1.0 | 1.0 |

(*) added as a 25% (w/w) solution in Ether-1.

Evaluation and Results

The free radical curable liquids COMP-4 and INV-5 to INV-11 were coated on a PET100 substrate using a bar coater and a 10 mm wired bar. Each coated sample was cured using a Fusion DRSE-120 conveyer, equipped with a Fusion VPS/1600 lamp (D-bulb), which transported the samples under the UV-lamp on a conveyer belt at a speed of 20 m/min. The curing speed and the viscosity were determined.

The results are summarized in Table 10.

TABLE 10

| Radiation curable composition | Curing speed (% of the maximum output) | Viscosity (mPa · s) |
|---|---|---|
| INV-5 | 50 | 20.8 |
| INV-6 | 80 | 14.1 |
| INV-7 | 70 | 32.4 |
| INV-8 | 80 | 11.4 |
| INV-9 | 65 | 13.5 |
| INV-10 | 65 | 12.7 |
| INV-11 | 65 | 16.9 |
| COMP-4 | 65 | 12.7 |

From Table 10, it becomes apparent that the polymerizable Norrish type I photoinitiators, according to a preferred embodiment of the present invention, result in highly sensitive radiation curable compositions, comparable to state-of-the-art initiating systems.

Example 9

This example illustrates the photoreactivity of polymerizable Norrish type II initiators, according to a preferred embodiment of the present invention, in combination with a polymerizable Norrish type I initiator and a polymerizable coinitiator.

Preparation of Radiation Curable Compositions

The comparative radiation curable composition COMP-5 and inventive radiation curable compositions INV-12 to INV-22 were prepared according to Table 11 and Table 12. The weight % (wt %) was based on the total weight of the radiation curable compositions. Dibutyl phthalate was added to the radiation curable compositions as an internal reference to allow analysis of extractable residues. The pre-formulations, prepared in the preceding examples were directly used in the radiation curable compositions.

TABLE 11

| wt % of | INV-12 | INV-13 | INV-14 | INV-15 | INV-16 | INV-17 |
|---|---|---|---|---|---|---|
| Ether-1 | 26.0 | 22.5 | 14.0 | 21.5 | 10.0 | 9.0 |
| M600 | 20.0 | 20.0 | 20.0 | 20.0 | 20.0 | 20.0 |
| FVEEA-8 | 13.0 | — | — | — | — | — |
| FVEEA-9 | — | 16.5 | — | — | — | — |
| FVEEA-10 | — | — | 25.0 | — | — | — |
| FVEEA-11 | — | — | — | 17.5 | — | — |
| FVEEA-12 | — | — | — | — | 29.0 | — |
| FVEEA-13 | — | — | — | — | — | 30.0 |
| STIN-5 (*) | 20.0 | 20.0 | 20.0 | 20.0 | 20.0 | 20.0 |
| COINI-1 (*) | 20.0 | 20.0 | 20.0 | 20.0 | 20.0 | 20.0 |
| Dibutyl phthalate | 1.0 | 1.0 | 1.0 | 1.0 | 1.0 | 1.0 |

TABLE 12

| wt % of | INV-18 | INV-19 | INV-20 | INV-21 | INV-22 | COMP-5 |
|---|---|---|---|---|---|---|
| Ether-1 | 17.0 | 21.5 | 17.0 | 11.5 | 13.0 | 9.0 |
| M600 | 20.0 | 20.0 | 20.0 | 20.0 | 20.0 | 20.0 |
| FVEEA-16 | 22.0 | — | — | — | — | — |
| FVEEA-18 | — | 17.5 | — | — | — | — |
| FVEEA-19 | — | — | 22.0 | — | — | — |
| FVEEA-14 | — | — | — | 27.5 | — | — |
| FVEEA-17 | — | — | — | — | 26.0 | — |
| STIN-5 (*) | 20.0 | 20.0 | 20.0 | 20.0 | 20.0 | 20.0 |
| COINI-1 (*) | 20.0 | 20.0 | 20.0 | 20.0 | 20.0 | 20.0 |
| Type II (*) | — | — | — | — | — | 30.0 |
| Dibutyl phthalate | 1.0 | 1.0 | 1.0 | 1.0 | 1.0 | 1.0 |

(*) added as a 25% (w/w) solution in Ether-1.

Evaluation and Results

The free radical curable compositions COMP-5 and INV-12 to INV-22 were coated on a PET100 substrate using a bar coater and a 10 mm wired bar. Each coated sample was cured using a Fusion DRSE-120 conveyer, equipped with a Fusion VPS/I600 lamp (D-bulb), which transported the samples under the UV-lamp on a conveyer belt at a speed of 20 m/min. The curing speed was determined.

The results are summarized in Table 13.

TABLE 13

| Radiation curable composition | Curing speed (% of the maximum output) |
|---|---|
| INV-12 | 170 |
| INV-13 | 150 |
| INV-14 | 65 |
| INV-15 | 140 |
| INV-16 | 60 |
| INV-17 | 55 |
| INV-18 | 140 |
| INV-19 | 150 |
| INV-20 | 200 |
| INV-21 | 180 |
| INV-22 | 70 |
| COMP-5 | 60 |

From Table 13, it becomes apparent that all Norrish type II initiators, according to a preferred embodiment of the present invention result in fully cured coatings under ambient atmosphere within a practical range. For the same spectral absorption, the curing speed is comparable to with state-of-the-art polymerizable initiators.

Example 10

This example illustrates the reduction of extractable residues by the use of photoinitiators according to a preferred embodiment of the present invention.

Evaluation and Results

The inventive radiation curable compositions INV-1, INV-5, INV-11 and INV-17 and the comparative radiation curable composition COMP-4 were coated on a PET100 substrate using a bar coater and a 10 μm wired bar. Each coated sample was cured using a Fusion DRSE-120 conveyer, equipped with a Fusion VPS/I600 lamp (D-bulb), which transported the samples under the UV-lamp on a conveyer belt at a speed of 20 m/min. The lamp was used at full power. The samples were cured under nitrogen inerting conditions. Before a coated sample was placed on the conveyer belt, the coated sample was mounted on a metal plate and on top of the plate a metal frame of 1 cm height with a non UV-absorbing quartz glass window was placed, so that a sealed chamber was formed with the coated sample inside. Then, the trapped air in the chamber was replaced by nitrogen gas by introducing pure nitrogen gas into the chamber for 30 seconds. All cured samples were found to be fully cured.

Two samples of 7.068 cm$^2$ of COMP-4 and INV-1, INV-5, INV-11 and INV-17 were put into a 50 mL beaker and extracted with 4.5 mL acetonitrile, using ultrasound for 30 minutes. The extract was transferred into a 5 mL volumetric flask. The samples were rinsed twice with a small amount of acetonitrile and the rinsing solvent was transferred into the 5 mL volumetric flask until the volume was adjusted to 5 mL. The solution was thoroughly mixed and filtered over a 0.45 mm filter. 10 mL of each sample was injected on the HPLC.

The concentration was determined in comparison with a reference sample of a known concentration of each comparative and inventive initiator, eluted under the same conditions as the extracted samples.

A total coating weight of 10 g/m$^2$ was assumed for each sample.

An Alltime C18 5 mm column (150×3.2 mm), supplied by Alltech, was used. A flow rate of 0.5 mL/min was used at a temperature of 40° C. A DAD detector at 254 nm was used to detect the extracted initiators.

The HPLC-method used the same eluents composition according to Table 14 with water as Eluent A and CH$_3$CN as Eluent B for all samples.

TABLE 14

| Time (min) | % eluent A | % eluent B |
|---|---|---|
| 0 | 55 | 45 |
| 6 | 55 | 45 |
| 11 | 0 | 100 |
| 30 | 0 | 100 |
| 31 | 55 | 45 |
| 38 | 55 | 45 |

The results are summarized in Table 15.

TABLE 15

| Radiation curable composition | Initiator | Extractable amount of the initiator (mg/m$^2$) |
|---|---|---|
| INV-1 | INI-28 | 2.8 |
| INV-5 | INI-28 | 7.1 |
| INV-11 | INI-4 | 10.6 |
| INV-17 | INI-37 | 2.4 |
| COMP-4 | STIN-5 | 237.1 |

From Table 15, it should be clear that the initiators according to a preferred embodiment of the present invention significantly reduce the amount of extractable residues.

While preferred embodiments of the present invention have been described above, it is to be understood that variations and modifications will be apparent to those skilled in the art without departing the scope and spirit of the present invention. The scope of the present invention, therefore, is to be determined solely by the following claims.

The invention claimed is:
1. A polymerizable photoinitiator represented by Formula (I):

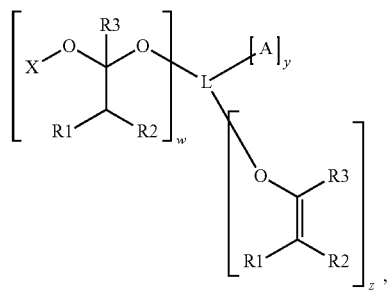

Formula (I)

wherein
R1, R2, and R3 are independently selected from the group consisting of a hydrogen, an optionally substituted alkyl group, and an optionally substituted aryl group, or R1 and R3 represent the necessary atoms to form a five to eight membered ring;
p, w, y, and z are all integers with y representing a value 1 to 6, p representing the sum of w and z wherein p also represents a value of 1 to 6, w=1 to (p−z), and z=0 to (p−w);
L represents an optionally substituted (p+y)-valent linking group including 1 to 14 carbon atoms;
A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, an allyl ester group, and a vinyl ester group; and
X represents a photoinitiating moiety including at least one group capable of initiating a free radical polymerization reaction upon exposure to actinic radiation.

2. The polymerizable photoinitiator according to claim 1, wherein R2 and R3 both represent hydrogen.

3. The polymerizable photoinitiator according to claim 2, wherein R1 represents hydrogen.

4. The polymerizable photoinitiator according to claim 1, wherein the photoinitiating moiety X includes at least one group selected from the group consisting of an optionally substituted benzophenone group, an optionally substituted thioxanthone group, a substituted or unsubstituted anthraquinone group, a camphor quinone group, an α-hydroxyalkylphenone group, an α-aminoalkylphenone group, an acylphosphine oxide group, a bisacyl phosphine oxide group, an acylphosphine sulfide group, a phenyl glyoxalate group, a benzoin ether group, a benzyl ketal group, an α-dialkoxyacetophenone group, a carbazolyl-O-acyl-oxime group, an α-haloarylketone group, and an α-haloaryl sulfone group.

5. The polymerizable photoinitiator according to claim 1, wherein the divalent linking group L is selected from the group consisting of an optionally substituted alkylene group and an aliphatic ether containing group.

6. A polymerizable photoinitiator according to Formula (Ib):

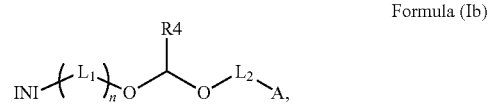

Formula (Ib)

wherein
- INI represents a group selected from the group consisting of an optionally substituted benzophenone group, an optionally substituted thioxanthone group, a substituted or unsubstituted anthraquinone group, a camphor quinone group, an α-hydroxyalkylphenone group, an α-aminoalkylphenone group, an acylphosphine oxide group, a bisacyl phosphine oxide group, an acylphosphine sulfide group, a phenyl glyoxalate group, a benzoin ether group, a benzyl ketal group, an α-dialkoxyacetophenone group, a carbazolyl-O-acyl-oxime group, an α-haloarylketone group, and an α-haloaryl sulfone group;
- $L_1$ and $L_2$ independently represent a substituted or unsubstituted divalent linking group including 1 to 14 carbon atoms;
- A represents a radically polymerizable functional group selected from the group consisting of an acrylate, a methacrylate, a styrene, an acryl amide, a methacryl amide, a maleate, a fumarate, an itaconate, an vinyl ether, an allyl ether, an allyl ester, and a vinyl ester;
- n represents 0 or 1; and
- R4 represents an optionally substituted alkyl group.

7. The polymerizable photoinitiator according to claim 6, wherein R4 represents a methyl group.

8. The polymerizable photoinitiator according to claim 6, wherein $L_2$ is selected from the group consisting of a substituted alkylene group, an unsubstituted alkylene group, and an aliphatic ether containing group.

9. The polymerizable photoinitiator according to claim 1, wherein the radically polymerizable group A is an acrylate group.

10. A radiation curable composition comprising:
the polymerizable photoinitiator according to Formula (I), as defined by claim 1.

11. The radiation curable composition according to claim 10, further comprising at least one monomer according to Formula (II):

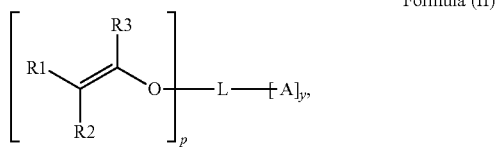

Formula (II)

wherein
- R1, R2, and R3 are independently selected from the group consisting of a hydrogen, an optionally substituted alkyl group, and an optionally substituted aryl group, or R1 and R3 represent the necessary atoms to form a five to eight membered ring;
- p is an integer representing a value of 1 to 6
- y is an integer representing a value of 1 to 6;
- L represents an optionally substituted (p+y)-valent linking group including 1 to 14 carbon atoms; and
- A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, an allyl ester group, and a vinyl ester group.

12. The radiation curable composition according to claim 11, wherein the monomer according to Formula (II) is 2-(2-vinyloxyethoxy)ethyl acrylate.

13. The radiation curable composition according to claim 11, wherein the radiation curable composition is a radiation curable ink.

14. The radiation curable composition according to claim 11, wherein the radiation curable composition is a radiation curable inkjet ink composition.

15. The radiation curable composition according to claim 11, wherein the radiation curable composition is substantially free of organic solvent.

16. The radiation curable composition according to claim 11, wherein the radiation curable composition is a radiation curable ink which is substantially free of organic solvent.

17. A radiation curable composition comprising:
the polymerizable photoinitiator according to Formula (Ib), as defined by claim 6.

18. The radiation curable composition according to claim 17, further comprising at least one monomer according to Formula (II):

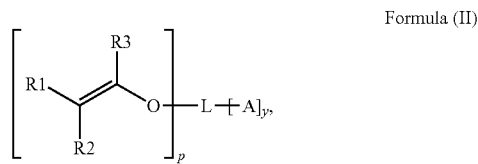

Formula (II)

wherein
- R1, R2, and R3 are independently selected from the group consisting of a hydrogen, an optionally substituted alkyl group, and an optionally substituted aryl group, or R1 and R3 represent the necessary atoms to form a five to eight membered ring;
- p is an integer representing a value of 1 to 6
- y is an integer representing a value of 1 to 6;
- L represents an optionally substituted (p+y)-valent linking group including 1 to 14 carbon atoms; and
- A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, an allyl ester group, and a vinyl ester group.

19. The radiation curable composition according to claim 18, wherein the monomer according to Formula (II) is 2-(2-vinyloxyethoxy)ethyl acrylate.

20. The radiation curable composition according to claim 18, wherein the radiation curable composition is a radiation curable ink.

21. The radiation curable composition according to claim 18, wherein the radiation curable composition is a radiation curable inkjet ink composition.

22. The radiation curable composition according to claim 18, wherein the radiation curable composition is substantially free of organic solvent.

23. The radiation curable composition according to claim 18, wherein the radiation curable composition is a radiation curable ink which is substantially free of organic solvent.

24. A method of preparing a polymerizable photoinitiator comprising the steps of:
a) providing a monomer according to Formula (II):

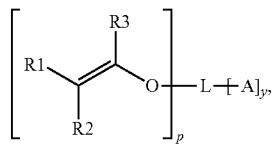

Formula (II)

wherein
- R1, R2, and R3 are independently selected from the group consisting of a hydrogen, an optionally substituted alkyl group, and an optionally substituted aryl group, or R1 and R3 represent the necessary atoms to form a five to eight membered ring;
- p is an integer representing a value of 1 to 6
- y is an integer representing a value of 1 to 6;
- L represents an optionally substituted (p+y)-valent linking group including 1 to 14 carbon atoms; and
- A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, an allyl ester group, and a vinyl ester group;

b) providing one or more photoinitiators including at least one hydroxyl group; and c) catalyzing the reaction between the monomer and the photoinitiator with a catalyst to a polymerizable photoinitiator according to the Formula (I) or Formula (1b):

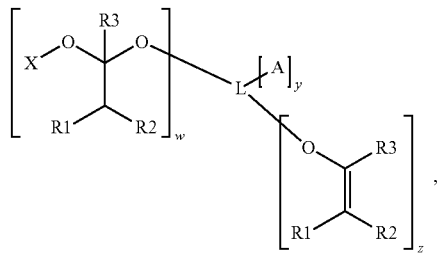

Formula (I)

wherein
- R1, R2, and R3 are independently selected from the group consisting of a hydrogen, an optionally substituted alkyl group, and an optionally substituted aryl group, or R1 and R3 represent the necessary atoms to form a five to eight membered ring;
- p, w, y, and z are all integers with y representing a value 1 to 6, p representing the sum of w and z wherein p also represents a value of 1 to 6, w=1 to (p−z), and z=0 to (p−w);
- L represents an optionally substituted (p+y)-valent linking group including 1 to 14 carbon atoms;
- A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, an allyl ester group, and a vinyl ester group; and
- X represents a photo initiating moiety including at least one group capable of initiating a free radical polymerization reaction upon exposure to actinic radiation;

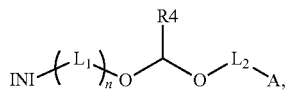

Formula (Ib)

wherein
- INI represents a group selected from the group consisting of an optionally substituted benzophenone group, an optionally substituted thioxanthone group, a substituted or unsubstituted anthraquinone group, a camphor quinone group, an α-hydroxyalkylphenone group, an α-aminoalkylphenone group, an acylphosphine oxide group, a bisacyl phosphine oxide group, an acylphosphine sulfide group, a phenyl glyoxalate group, a benzoin ether group, a benzyl ketal group, an α-dialkoxyacetophenone group, a carbazolyl-O-acyl-oxime group, an α-haloarylketone group, and an α-haloaryl sulfone group;
- $L_1$ and $L_2$ independently represent a substituted or unsubstituted divalent linking group including 1 to 14 carbon atoms;
- A represents a radically polymerizable functional group selected from the group consisting of an acrylate, a methacrylate, a styrene, an acryl amide, a methacryl amide, a maleate, a fumarate, an itaconate, an vinyl ether, an allyl ether, an allyl ester, and a vinyl ester;
- n represents 0 or 1; and
- R4 represents an optionally substituted alkyl group.

25. The method according to claim 24, wherein the catalyst is selected from the group consisting of trifluoroacetic acid, trichloroacetic acid, pyridinium tosylate, crosslinked poly (vinylpyridine) hydrochloride, poly(vinylpyridinium) tosylate, and sulfonic acid substituted ion exchangers.

26. The method according to claim 24, wherein the reaction is performed in the absence of an organic solvent.

* * * * *

UNITED STATES PATENT AND TRADEMARK OFFICE
CERTIFICATE OF CORRECTION

PATENT NO.        : 8,492,452 B2
APPLICATION NO.   : 13/129413
DATED             : July 23, 2013
INVENTOR(S)       : Johan Loccufier et al.

It is certified that error appears in the above-identified patent and that said Letters Patent is hereby corrected as shown below:

Title Page:

Item (75) please correct the second inventor's name as follows:

Luc Vanmaele, Lochristi (BE)

Signed and Sealed this
Seventh Day of January, 2014

Margaret A. Focarino
*Commissioner for Patents of the United States Patent and Trademark Office*